US009649206B2

(12) United States Patent
Bédard

(10) Patent No.: US 9,649,206 B2
(45) Date of Patent: May 16, 2017

(54) CONTROL DEVICE AND SYSTEM FOR CONTROLLING AN ACTUATED PROSTHESIS

(71) Applicant: Victhom Laboratory Inc., Laval (CA)

(72) Inventor: Stéphane Bédard, Québec (CA)

(73) Assignee: Victhom Laboratory Inc., Quebec (CA)

( * ) Notice: Subject to any disclaimer, the term of this patent is extended or adjusted under 35 U.S.C. 154(b) by 0 days.

(21) Appl. No.: 13/944,778

(22) Filed: Jul. 17, 2013

(65) Prior Publication Data

US 2013/0297041 A1    Nov. 7, 2013

Related U.S. Application Data

(60) Continuation of application No. 12/987,801, filed on Jan. 10, 2011, now abandoned, which is a
(Continued)

(51) Int. Cl.
*A61F 2/70* (2006.01)
*A61F 2/64* (2006.01)
(Continued)

(52) U.S. Cl.
CPC ............... *A61F 2/68* (2013.01); *A61F 2/644* (2013.01); *A61F 2/6607* (2013.01); *A61F 2002/607* (2013.01); *A61F 2002/6614* (2013.01); *A61F 2002/701* (2013.01); *A61F 2002/704* (2013.01); *A61F 2002/705* (2013.01); *A61F 2002/762* (2013.01); *A61F 2002/763* (2013.01); *A61F 2002/7625* (2013.01);
(Continued)

(58) Field of Classification Search
None
See application file for complete search history.

(56) References Cited

U.S. PATENT DOCUMENTS 909,859 A    1/1909  Apgar
2,475,373 A  7/1949  Catranis
(Continued)

FOREIGN PATENT DOCUMENTS

CA    2405356    10/2001
CA    2494365    3/2004
(Continued)

OTHER PUBLICATIONS

English language translation of SU 1 447 366 Al (Dec. 30, 1988).*
(Continued)

*Primary Examiner* — David H Willse
(74) *Attorney, Agent, or Firm* — Knobbe, Martens, Olson & Bear, LLP

(57) ABSTRACT

A motorized prosthetic device includes a joint member, a limb member, a pressure sensor, and a kinematic sensor. The pressure sensor indicates interaction between the motorized prosthetic device and the ground and the kinematic sensor measures torque at the joint member. A controller receives data from the pressure sensor and kinematic sensor and calculates a control signal based at least on the received data. An electrical motor receives the control signal and operates an actuator in accordance with the received control signal.

20 Claims, 20 Drawing Sheets

Related U.S. Application Data continuation of application No. 11/270,684, filed on Nov. 9, 2005, now Pat. No. 7,867,284, which is a division of application No. 10/600,725, filed on Jun. 20, 2003, now Pat. No. 7,147,667.

(60) Provisional application No. 60/405,281, filed on Aug. 22, 2002, provisional application No. 60/424,261, filed on Nov. 6, 2002, provisional application No. 60/453,556, filed on Mar. 11, 2003.

(51) Int. Cl.
    *A61F 2/66* (2006.01)
    *A61F 2/68* (2006.01)
    *A61F 2/76* (2006.01)
    *A61F 2/60* (2006.01)

(52) U.S. Cl.
    CPC ............... *A61F 2002/7635* (2013.01); *A61F 2002/7645* (2013.01); *A61F 2002/7685* (2013.01)

(56) References Cited

U.S. PATENT DOCUMENTS

| | | |
|---|---|---|
| 2,568,051 A | 9/1951 | Catranis |
| 2,619,652 A | 12/1952 | Vesper |
| 2,859,451 A | 11/1958 | Mauch |
| 3,316,558 A | 5/1967 | Mortensen |
| 3,417,409 A | 12/1968 | Prahl |
| 3,501,776 A | 3/1970 | Beeker et al. |
| 3,589,134 A | 6/1971 | Hackmann |
| 3,659,294 A | 5/1972 | Glabiszewski |
| 3,701,368 A | 10/1972 | Stern |
| 3,791,375 A | 2/1974 | Pfeiffer |
| 3,820,168 A | 6/1974 | Horvath |
| 3,866,246 A | 2/1975 | Seamone et al. |
| 3,871,032 A | 3/1975 | Karas |
| 3,953,900 A | 5/1976 | Thompson |
| 3,995,324 A | 12/1976 | Burch |
| 4,005,496 A | 2/1977 | Wilkes |
| 4,023,215 A | 5/1977 | Moore |
| 4,030,141 A | 6/1977 | Graupe |
| 4,064,569 A | 12/1977 | Campbell |
| 4,065,815 A | 1/1978 | Sen-Jung |
| 4,100,918 A | 7/1978 | Glancy |
| 4,179,759 A | 12/1979 | Smith |
| 4,209,860 A | 7/1980 | Graupe |
| 4,212,087 A | 7/1980 | Mortensen |
| 4,310,932 A | 1/1982 | Nader et al. |
| 4,314,379 A | 2/1982 | Tanie et al. |
| 4,354,676 A | 10/1982 | Ariel |
| 4,386,891 A | 6/1983 | Riefel et al. |
| 4,387,472 A | 6/1983 | Wilson |
| 4,433,679 A | 2/1984 | Mauldin et al. |
| 4,458,367 A | 7/1984 | May |
| 4,518,307 A | 5/1985 | Bloch |
| 4,521,924 A | 6/1985 | Jacobsen et al. |
| 4,556,956 A | 12/1985 | Dickenson et al. |
| 4,558,704 A | 12/1985 | Petrofsky |
| 4,569,352 A | 2/1986 | Petrofsky et al. |
| 4,578,083 A | 3/1986 | Williams |
| 4,579,558 A | 4/1986 | Ramer |
| 4,600,357 A | 7/1986 | Coules |
| 4,602,619 A | 7/1986 | Wolf et al. |
| 4,617,920 A | 10/1986 | Carsalade |
| 4,649,934 A | 3/1987 | Fraser et al. |
| 4,652,266 A | 3/1987 | Truesdell |
| 4,657,000 A | 4/1987 | Hepburn |
| 4,657,470 A | 4/1987 | Clarke et al. |
| 4,685,926 A | 8/1987 | Haupt |
| 4,685,927 A | 8/1987 | Haupt |
| 4,711,242 A | 12/1987 | Petrofsky |
| 4,726,404 A | 2/1988 | Haber et al. |
| 4,730,625 A | 3/1988 | Fraser et al. |
| 4,760,850 A | 8/1988 | Phillips et al. |
| 4,770,662 A | 9/1988 | Giampapa |
| 4,776,326 A | 10/1988 | Young et al. |
| 4,776,852 A | 10/1988 | Bubic |
| 4,790,522 A | 12/1988 | Drutchas |
| 4,795,474 A | 1/1989 | Horvath |
| 4,805,455 A | 2/1989 | DelGiorno et al. |
| 4,808,187 A | 2/1989 | Patterson et al. |
| 4,814,661 A | 3/1989 | Ratzlaff et al. |
| 4,838,251 A | 6/1989 | Chignon et al. |
| 4,843,921 A | 7/1989 | Kremer |
| 4,854,428 A | 8/1989 | Horvath |
| 4,865,024 A | 9/1989 | Hensley et al. |
| 4,872,803 A | 10/1989 | Asakawa |
| 4,876,944 A | 10/1989 | Wilson et al. |
| 4,878,913 A | 11/1989 | Aebischer et al. |
| 4,892,554 A | 1/1990 | Robinson |
| 4,893,648 A | 1/1990 | Horvath |
| 4,919,418 A | 4/1990 | Miller |
| 4,928,676 A | 5/1990 | Pansiera |
| 4,944,755 A | 7/1990 | Hennequin et al. |
| 4,958,705 A | 9/1990 | Horvath |
| 4,989,161 A | 1/1991 | Oaki |
| 4,994,086 A | 2/1991 | Edwards |
| 5,020,790 A | 6/1991 | Beard et al. |
| 5,033,291 A | 7/1991 | Podoloff et al. |
| 5,044,360 A | 9/1991 | Janke |
| 5,062,673 A | 11/1991 | Mimura |
| 5,062,856 A | 11/1991 | Sawamura et al. |
| 5,062,857 A | 11/1991 | Berringer et al. |
| 5,086,785 A | 2/1992 | Gentile et al. |
| 5,092,902 A | 3/1992 | Adams et al. |
| 5,112,296 A | 5/1992 | Beard et al. |
| 5,112,356 A | 5/1992 | Harris et al. |
| 5,133,773 A | 7/1992 | Sawamura et al. |
| 5,133,774 A | 7/1992 | Sawamura et al. |
| 5,139,525 A | 8/1992 | Kristinsson |
| 5,153,496 A | 10/1992 | LaForge |
| 5,174,168 A | 12/1992 | Takagi et al. |
| 5,181,931 A | 1/1993 | Van de Veen |
| 5,197,488 A | 3/1993 | Kovacevic |
| 5,201,772 A | 4/1993 | Maxwell |
| 5,217,500 A | 6/1993 | Phillips |
| 5,219,365 A | 6/1993 | Sabolich |
| 5,230,672 A | 7/1993 | Brown et al. |
| 5,246,465 A | 9/1993 | Rincoe et al. |
| 5,252,102 A | 10/1993 | Singer et al. |
| 5,252,901 A | 10/1993 | Ozawa et al. |
| 5,253,656 A | 10/1993 | Rincoe |
| 5,265,890 A | 11/1993 | Balsells |
| 5,277,281 A | 1/1994 | Carlson et al. |
| 5,282,460 A * | 2/1994 | Boldt .......................... 601/5 |
| 5,284,330 A | 2/1994 | Carlson et al. |
| 5,314,498 A | 5/1994 | Gramnas |
| 5,323,650 A | 6/1994 | Fullen et al. |
| 5,327,790 A | 7/1994 | Levin et al. |
| 5,336,269 A | 8/1994 | Smits |
| 5,357,696 A | 10/1994 | Gray et al. |
| 5,376,128 A | 12/1994 | Bozeman, Jr. |
| 5,376,133 A | 12/1994 | Gramnas |
| 5,376,137 A | 12/1994 | Shorter et al. |
| 5,376,138 A | 12/1994 | Bouchard et al. |
| 5,376,141 A | 12/1994 | Phillips |
| 5,382,373 A | 1/1995 | Carlson et al. |
| 5,383,939 A | 1/1995 | James |
| 5,394,132 A | 2/1995 | Poil |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A | 5/1995 | Haslam, II et al. |
| 5,422,558 A | 6/1995 | Stewart |
| 5,437,611 A | 8/1995 | Stern |
| 5,443,521 A | 8/1995 | Knoth et al. |
| 5,443,524 A | 8/1995 | Sawamura et al. |
| 5,443,528 A | 8/1995 | Allen |
| 5,455,497 A | 10/1995 | Hirose et al. |
| 5,472,412 A | 12/1995 | Knoth |

(56) References Cited

U.S. PATENT DOCUMENTS

| | | |
|---|---|---|
| 5,476,441 A | 12/1995 | Durfee et al. |
| 5,484,389 A | 1/1996 | Stark et al. |
| 5,504,415 A | 4/1996 | Podrazhansky et al. |
| D372,536 S | 8/1996 | Grifka |
| 5,545,232 A | 8/1996 | Van de Veen |
| 5,545,233 A | 8/1996 | Fitzlaff |
| 5,551,525 A | 9/1996 | Pack et al. |
| 5,563,458 A | 10/1996 | Ericson |
| 5,566,479 A | 10/1996 | Gray et al. |
| 5,571,205 A | 11/1996 | James |
| 5,571,210 A | 11/1996 | Lindh |
| 5,571,212 A | 11/1996 | Cornelius |
| 5,571,213 A | 11/1996 | Allen |
| 5,583,476 A | 12/1996 | Langford et al. |
| 5,586,557 A | 12/1996 | Nelson et al. |
| 5,624,389 A | 4/1997 | Zepf |
| 5,642,096 A | 6/1997 | Leyerer et al. |
| 5,645,590 A | 7/1997 | Van de Veen |
| 5,645,752 A | 7/1997 | Weiss et al. |
| 5,650,704 A | 7/1997 | Pratt et al. |
| 5,656,915 A | 8/1997 | Eaves |
| D383,542 S | 9/1997 | Wellershaus et al. |
| 5,662,693 A | 9/1997 | Johnson et al. |
| 5,670,077 A | 9/1997 | Carlson et al. |
| 5,678,448 A | 10/1997 | Fullen et al. |
| 5,683,615 A | 11/1997 | Munoz |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,728,170 A | 3/1998 | Becker et al. |
| 5,728,174 A | 3/1998 | Fitzlaff |
| 5,746,774 A | 5/1998 | Kramer et al. |
| 5,749,533 A | 5/1998 | Daniels |
| 5,755,812 A | 5/1998 | Becker et al. |
| 5,755,813 A | 5/1998 | Krukenberg |
| 5,779,735 A | 7/1998 | Molino |
| 5,800,561 A | 9/1998 | Rodriguez |
| 5,800,568 A | 9/1998 | Atkinson et al. |
| 5,810,752 A | 9/1998 | Grifka |
| 5,823,309 A | 10/1998 | Gopalswamy et al. |
| D402,368 S | 12/1998 | Holzapfel |
| 5,842,547 A | 12/1998 | Carlson et al. |
| D407,490 S | 3/1999 | Zepf et al. |
| 5,878,851 A | 3/1999 | Carlson et al. |
| 5,888,212 A | 3/1999 | Petrofsky et al. |
| 5,888,213 A | 3/1999 | Sears et al. |
| 5,888,236 A | 3/1999 | Van de Veen |
| 5,888,239 A | 3/1999 | Wellershaus et al. |
| 5,888,246 A | 3/1999 | Gow |
| 5,893,891 A | 4/1999 | Zahedi |
| 5,895,430 A | 4/1999 | O'Connor |
| 5,899,869 A | 5/1999 | Barrack, Jr. et al. |
| 5,900,184 A | 5/1999 | Weiss et al. |
| 5,906,767 A | 5/1999 | Karol et al. |
| 5,919,149 A | 7/1999 | Allum |
| 5,929,332 A | 7/1999 | Brown |
| 5,941,913 A | 8/1999 | Woolnough et al. |
| 5,947,238 A | 9/1999 | Jolly et al. |
| 5,948,021 A | 9/1999 | Radcliffe |
| 5,955,667 A | 9/1999 | Fyfe |
| 5,957,981 A | 9/1999 | Gramnas |
| 5,960,918 A | 10/1999 | Moser et al. |
| 5,967,273 A | 10/1999 | Hampton |
| 5,972,035 A | 10/1999 | Blatchford |
| 5,982,156 A | 11/1999 | Weimer et al. |
| 5,984,972 A | 11/1999 | Huston et al. |
| 5,998,930 A | 12/1999 | Upadhyay et al. |
| 6,006,412 A | 12/1999 | Bergmann et al. |
| 6,007,582 A | 12/1999 | May |
| RE36,521 E | 1/2000 | Hiemisch |
| 6,039,091 A | 3/2000 | Rodgers et al. |
| 6,061,577 A | 5/2000 | Andrieu et al. |
| 6,080,123 A | 6/2000 | Pansiera |
| 6,086,616 A | 7/2000 | Okuda et al. |
| 6,091,977 A | 7/2000 | Tarjan et al. |
| 6,093,162 A | 7/2000 | Fairleigh et al. |
| 6,095,486 A | 8/2000 | Ivers et al. |
| 6,113,642 A | 9/2000 | Petrofsky et al. |
| 6,117,177 A | 9/2000 | Chen et al. |
| 6,129,690 A | 10/2000 | Hamlin et al. |
| 6,139,586 A | 10/2000 | Wagner et al. |
| 6,165,226 A | 12/2000 | Wagner |
| 6,168,634 B1 | 1/2001 | Schmitz |
| 6,183,425 B1 | 2/2001 | Whalen et al. |
| 6,187,051 B1 | 2/2001 | van de Veen |
| 6,187,052 B1 | 2/2001 | Molino et al. |
| D439,339 S | 3/2001 | Sawatzki |
| 6,195,921 B1 | 3/2001 | Truong |
| 6,206,932 B1 | 3/2001 | Johnson |
| 6,206,933 B1 | 3/2001 | Shorter et al. |
| 6,206,934 B1 | 3/2001 | Phillips |
| 6,241,775 B1 | 6/2001 | Blatchford |
| D446,304 S | 8/2001 | Sawatzki |
| 6,301,964 B1 | 10/2001 | Fyfe et al. |
| 6,342,076 B1 | 1/2002 | Lundborg |
| 6,350,286 B1 | 2/2002 | Atkinson et al. |
| 6,352,144 B1 | 3/2002 | Brooks |
| 6,361,570 B1 | 3/2002 | Gow |
| 6,373,152 B1 | 4/2002 | Wang et al. |
| 6,378,190 B2 | 4/2002 | Akeel |
| 6,379,393 B1 | 4/2002 | Mavroidis et al. |
| 6,395,193 B1 | 5/2002 | Kintz et al. |
| 6,409,695 B1 | 6/2002 | Connelly |
| 6,423,098 B1 | 7/2002 | Biedermann |
| 6,425,925 B1 | 7/2002 | Grundei |
| 6,430,843 B1 | 8/2002 | Potter et al. |
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,485,519 B2 | 11/2002 | Meyers et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,517,858 B1 | 2/2003 | Le Moel et al. |
| 6,522,266 B1 | 2/2003 | Soehren et al. |
| 6,537,322 B1 | 3/2003 | Johnson et al. |
| 6,543,987 B2 | 4/2003 | Ehrat |
| 6,587,728 B2 | 7/2003 | Fang et al. |
| 6,589,287 B2 | 7/2003 | Lundborg |
| 6,599,439 B2 | 7/2003 | Iyengar et al. |
| 6,602,295 B1 | 8/2003 | Doddroe et al. |
| 6,610,101 B2 | 8/2003 | Herr et al. |
| 6,613,097 B1 | 9/2003 | Cooper |
| 6,645,252 B2 | 11/2003 | Asai et al. |
| 6,663,673 B2 | 12/2003 | Christensen |
| 6,671,531 B2 | 12/2003 | Al-Ali et al. |
| 6,679,920 B2 | 1/2004 | Biedermann et al. |
| 6,695,885 B2 | 2/2004 | Schulman et al. |
| 6,704,024 B2 | 3/2004 | Robotham et al. |
| 6,704,582 B2 | 3/2004 | Le-Faucheur et al. |
| 6,719,806 B1 | 4/2004 | Zahedi et al. |
| 6,733,180 B2 | 5/2004 | Nakamura |
| 6,740,123 B2 | 5/2004 | Davalli et al. |
| 6,740,125 B2 | 5/2004 | Mosler |
| 6,743,260 B2 | 6/2004 | Townsend et al. |
| 6,755,870 B1 | 6/2004 | Biedermann et al. |
| 6,761,743 B1 | 7/2004 | Johnson |
| 6,764,520 B2 | 7/2004 | Deffenbaugh et al. |
| 6,764,521 B2 | 7/2004 | Molino et al. |
| 6,767,370 B1 | 7/2004 | Mosler et al. |
| 6,770,045 B2 | 8/2004 | Naft et al. |
| 6,780,343 B2 | 8/2004 | Hata et al. |
| 6,805,677 B2 | 10/2004 | Simmons |
| 6,811,571 B1 | 11/2004 | Phillips |
| 6,813,582 B2 | 11/2004 | Levi et al. |
| 6,855,170 B2 | 2/2005 | Gramnas |
| 6,875,241 B2 | 4/2005 | Christesen |
| 6,876,135 B2 | 4/2005 | Pelrine et al. |
| 6,908,488 B2 | 6/2005 | Passivaara et al. |
| 6,910,331 B2 * | 6/2005 | Asai et al. ............. 60/517 |
| 6,918,308 B2 | 7/2005 | Biedermann |

(56) References Cited

U.S. PATENT DOCUMENTS

| | | |
|---|---|---|
| 6,966,882 B2 | 11/2005 | Horst |
| 7,029,500 B2 | 4/2006 | Martin |
| 7,042,197 B2 | 5/2006 | Turner et al. |
| 7,063,727 B2 | 6/2006 | Phillips et al. |
| 7,066,896 B1 | 6/2006 | Kiselik |
| 7,066,964 B2 | 6/2006 | Wild |
| 7,101,487 B2 | 9/2006 | Hsu et al. |
| 7,118,601 B2 | 10/2006 | Yasui et al. |
| 7,137,998 B2 | 11/2006 | Bédard et al. |
| 7,147,667 B2 | 12/2006 | Bédard et al. |
| 7,150,762 B2 | 12/2006 | Caspers |
| 7,164,967 B2 | 1/2007 | Etienne-Cummings et al. |
| 7,182,738 B2 | 2/2007 | Bonutti et al. |
| 7,198,071 B2 | 4/2007 | Bisbee, III et al. |
| 7,209,788 B2 | 4/2007 | Nicolelis et al. |
| 7,279,009 B2 | 10/2007 | Herr et al. |
| 7,295,892 B2 | 11/2007 | Herr et al. |
| 7,308,333 B2 | 12/2007 | Kern et al. |
| 7,314,490 B2 | 1/2008 | Bedard et al. |
| 7,381,192 B2 | 6/2008 | Brodard et al. |
| 7,396,337 B2 | 7/2008 | McBean et al. |
| 7,410,338 B2 | 8/2008 | Schiele et al. |
| 7,410,471 B1 | 8/2008 | Campbell et al. |
| 7,431,737 B2 | 10/2008 | Ragnarsdottir et al. |
| 7,455,696 B2 | 11/2008 | Bisbee, III et al. |
| 7,485,152 B2 | 2/2009 | Haynes et al. |
| 7,531,006 B2 | 5/2009 | Clausen et al. |
| 7,552,664 B2 | 6/2009 | Bulatowicz |
| 7,575,602 B2 | 8/2009 | Amirouche et al. |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,655,050 B2 | 2/2010 | Palmer et al. |
| 7,691,154 B2 | 4/2010 | Asgeirsson et al. |
| 7,736,394 B2 | 6/2010 | Bédard et al. |
| 7,799,091 B2 | 9/2010 | Herr et al. |
| 7,811,333 B2 | 10/2010 | Jónsson et al. |
| 7,811,334 B2 | 10/2010 | Ragnarsdottir et al. |
| 7,815,689 B2 | 10/2010 | Bédard et al. |
| 7,867,284 B2 | 1/2011 | Bédard et al. |
| 7,896,927 B2 | 3/2011 | Clausen et al. |
| 7,918,808 B2 | 4/2011 | Simmons |
| 7,942,935 B2 | 5/2011 | Iversen et al. |
| 7,955,398 B2 | 6/2011 | Bédard et al. |
| 8,048,007 B2 | 11/2011 | Roy |
| 8,048,172 B2 | 11/2011 | Jonsson et al. |
| 8,057,550 B2 | 11/2011 | Clausen et al. |
| 8,083,807 B2 | 12/2011 | Auberger et al. |
| 8,109,890 B2 | 2/2012 | Kamiar et al. |
| 8,142,370 B2 | 3/2012 | Weinberg et al. |
| 8,231,687 B2 | 7/2012 | Bedard et al. |
| 8,323,354 B2 | 12/2012 | Bédard et al. |
| 8,403,997 B2 | 3/2013 | Sykes et al. |
| 8,435,309 B2 | 5/2013 | Gilbert et al. |
| 8,551,184 B1 | 10/2013 | Herr |
| 8,657,886 B2 | 2/2014 | Clausen et al. |
| 8,702,811 B2 | 4/2014 | Ragnarsdottir et al. |
| 8,801,802 B2 | 8/2014 | Oddsson et al. |
| 8,814,949 B2 | 8/2014 | Gramnaes |
| 8,852,292 B2 | 10/2014 | Ragnarsdottir et al. |
| 8,986,397 B2 | 3/2015 | Bédard et al. |
| 2001/0029400 A1 | 10/2001 | Deffenbaugh et al. |
| 2002/0007690 A1 | 1/2002 | Song et al. |
| 2002/0052663 A1 | 5/2002 | Herr et al. |
| 2002/0079857 A1 | 6/2002 | Ishii et al. |
| 2002/0087216 A1 | 7/2002 | Atkinson et al. |
| 2002/0198604 A1 | 12/2002 | Schulman et al. |
| 2003/0019700 A1 | 1/2003 | Wittig |
| 2003/0120183 A1* | 6/2003 | Simmons ............... 600/595 |
| 2004/0064195 A1 | 4/2004 | Herr |
| 2004/0078299 A1 | 4/2004 | Down-Logan et al. |
| 2004/0083007 A1 | 4/2004 | Molino et al. |
| 2004/0167638 A1 | 8/2004 | Caspers |
| 2004/0193286 A1 | 9/2004 | Grundei |
| 2005/0107889 A1 | 5/2005 | Bédard et al. |
| 2005/0216097 A1 | 9/2005 | Rifkin |
| 2006/0069336 A1 | 3/2006 | Krebs et al. |
| 2006/0135883 A1 | 6/2006 | Jonsson et al. |
| 2006/0184280 A1 | 8/2006 | Oddsson et al. |
| 2006/0249315 A1 | 11/2006 | Herr et al. |
| 2006/0259153 A1 | 11/2006 | Harn et al. |
| 2007/0016329 A1 | 1/2007 | Herr et al. |
| 2007/0043449 A1 | 2/2007 | Herr et al. |
| 2007/0123997 A1 | 5/2007 | Herr et al. |
| 2007/0162152 A1 | 7/2007 | Herr et al. |
| 2008/0004718 A1 | 1/2008 | Mosler |
| 2008/0046096 A1 | 2/2008 | Bédard et al. |
| 2008/0306612 A1 | 12/2008 | Mosler |
| 2009/0030530 A1 | 1/2009 | Martin |
| 2010/0113980 A1 | 5/2010 | Herr et al. |
| 2010/0131101 A1 | 5/2010 | Engeberg et al. |
| 2010/0262260 A1 | 10/2010 | Bedard et al. |
| 2010/0324456 A1 | 12/2010 | Jónsson et al. |
| 2010/0324699 A1 | 12/2010 | Herr et al. |
| 2011/0106274 A1 | 5/2011 | Ragnarsdottir et al. |
| 2011/0125290 A1 | 5/2011 | Langlois |
| 2011/0130847 A1 | 6/2011 | Bédard et al. |
| 2011/0137429 A1 | 6/2011 | Bedard |
| 2011/0202144 A1 | 8/2011 | Palmer et al. |
| 2011/0295384 A1 | 12/2011 | Herr et al. |
| 2012/0016492 A1 | 1/2012 | Clausen |
| 2012/0209405 A1 | 8/2012 | Herr et al. |
| 2012/0283844 A1 | 11/2012 | Langlois |
| 2013/0035769 A1 | 2/2013 | Bédard et al. |
| 2013/0144402 A1 | 6/2013 | Clausen et al. |
| 2013/0204395 A1 | 8/2013 | Gramnaes |
| 2013/0268093 A1 | 10/2013 | Gilbert et al. |
| 2014/0081424 A1 | 3/2014 | Herr et al. |
| 2014/0243997 A1 | 8/2014 | Clausen et al. |
| 2014/0277586 A1 | 9/2014 | Clausen |
| 2015/0032225 A1 | 1/2015 | Oddsson et al. |
| 2015/0073566 A1 | 3/2015 | Ragnarsdottir et al. |

FOREIGN PATENT DOCUMENTS

| | | | |
|---|---|---|---|
| CA | 2543061 | 6/2005 | |
| CH | 543 277 | * 12/1973 | ............... A61F 2/74 |
| CH | 543277 | 12/1973 | |
| CN | 2043873 | 9/1989 | |
| CN | 1215614 | 5/1999 | |
| CN | 2400072 Y | 10/2000 | |
| DE | 3543291 | 6/1987 | |
| DE | 3923056 | 1/1991 | |
| DE | 3923057 | 1/1991 | |
| DE | 4229330 A1 | 3/1994 | |
| DE | 19859931 | 7/2000 | |
| EP | 0 358 056 | 3/1990 | |
| EP | 0 380 060 | 8/1990 | |
| EP | 0549855 A2 | 7/1993 | |
| EP | 0654254 | 5/1995 | |
| EP | 0902547 | 3/1999 | |
| EP | 1125825 | 1/2001 | |
| EP | 1107420 | 6/2001 | |
| EP | 1166726 A1 | 1/2002 | |
| EP | 1169982 A1 | 1/2002 | |
| EP | 1 410 780 | 4/2004 | |
| EP | 1 442 704 | 8/2004 | |
| EP | 1 547 567 | 6/2005 | |
| FR | 2293185 | 7/1976 | |
| FR | 2623086 | 5/1989 | |
| FR | 2 816 463 | 5/2002 | |
| GB | 2201260 | 8/1988 | |
| GB | 2244006 | 11/1991 | |
| GB | 2 260 495 | 4/1993 | |
| GB | 2301776 | 12/1996 | |
| GB | 2 302 949 A | 2/1997 | |
| GB | 2338653 | 12/1999 | |
| GB | 2343848 | 5/2000 | |
| GB | 2 367 753 A | * 4/2002 | ............... A61F 2/64 |
| GB | 2367753 | 4/2002 | |
| JP | 59-189843 | 10/1984 | |
| JP | 60-081530 | 5/1985 | |
| JP | 60-177102 | 9/1985 | |
| JP | 01-244748 | 9/1989 | |

(56) References Cited

FOREIGN PATENT DOCUMENTS

| JP | 03-181633 | 8/1991 |
|---|---|---|
| JP | 04-78337 | 3/1992 |
| JP | 05-123348 | 5/1993 |
| JP | 5-161668 | 6/1993 |
| JP | 11-000345 | 1/1999 |
| JP | 11056885 | 3/1999 |
| JP | 11-215793 | 8/1999 |
| JP | 2001-277175 | 10/2001 |
| JP | 2002-191654 A | 7/2002 |
| JP | 2005-500 | 1/2005 |
| JP | 2005-536317 | 12/2005 |
| KR | 2002/0041137 | 6/2002 |
| SU | 1731210 | 5/1992 |
| WO | WO 94/06374 | 3/1994 |
| WO | WO 94/09727 | 5/1994 |
| WO | WO 95/26171 | 10/1995 |
| WO | WO 96/39110 | 12/1996 |
| WO | WO 96/41599 | 12/1996 |
| WO | WO 97/00661 | 1/1997 |
| WO | WO 97/27822 | 8/1997 |
| WO | WO 98/38951 | 9/1998 |
| WO | WO 99/00075 | 1/1999 |
| WO | WO 99/05991 | 2/1999 |
| WO | WO 99/08621 | 2/1999 |
| WO | WO 99/55261 | 11/1999 |
| WO | WO 00/27318 | 5/2000 |
| WO | WO 00/38599 | 7/2000 |
| WO | WO 01/17466 | 3/2001 |
| WO | WO 01/72245 | 10/2001 |
| WO | WO 02/080825 | 10/2002 |
| WO | WO 03/003953 | 1/2003 |
| WO | WO 03/088373 | 10/2003 |
| WO | WO 2004/017890 | 3/2004 |
| WO | WO 2006/024876 A2 | 3/2006 |
| WO | WO 2007/025116 | 3/2007 |
| WO | WO 2010/027968 | 3/2010 |
| WO | WO 2013/006585 | 1/2013 |

OTHER PUBLICATIONS

CN 2043873U, published on Sep. 6, 1989: computer generated translation.*
Translation of CN 2043873 U (Sep. 6, 1989).*
Translation of JP 59-032453 A (Feb. 21, 1984).*
Translation of JP 59-071747 A (Apr. 23, 1984).*
Sigurdsson et al., "12th Nordic Baltic Conference on Biomedical Engineering and Medical Physics," Proceeding of the International Federation for Medical & Biological Engineering, Jun. 18-22, 2002, Reykjavik, Iceland, pp. 6.
Dietl, H., et al., Der Einsatz von Elektronik bei Prothesen zur Versorgung der unteren Extremität, Med. Orth. Tech 117 (1997), pp. 31-35.
Flowers, W.C., et al., "An Electrohydraulic Knee-Torque Controller for a Prosthesis Simulator", Journal of Biomechanical Engineering: Transactions of the ASME, Feb. 1977, pp. 3-8.
International Search Report for PCT/CA03/001120 mailed Mar. 2, 2004, 3 pages.
International Search Report for PCT/CA03/00937 mailed Dec. 3, 2003, 3 pages.
International Preliminary Report on Patentability for PCT/CA2008/000110 issued on Jul. 21, 2009, 7 pages.
International Search Report for PCT/CA2008/000110 mailed May 7, 2008, 2 pages.
Abbas, J.J., et al., "Neural Network Control of Functional Neuromuscular Stimulation Systems: Computer Simulation Studies", IEEE Transactions on Biomedical Engineering, Nov. 1995, 42(11):1117-1127.
Aminian, K., et al., "Estimation of Speed and Incline of Walking Using Neural Network", IEEE Transactions on Instrumentation and Measurement, vol. 44, No. 3, Jun. 1995, pp. 743-746.
Andrews, B.J., et al., "Hybrid FES Orthosis Incorporating Closed Loop Control and Sensory Feedback", J. Biomed. Eng. 1988, vol. 10, Apr. pp. 189-195.
Bachmann, E.R., "Inertial and Magnetic Tracking of Limb Segment Orientation for Inserting Humans into Synthetic Environments", Naval Postgraduate School, Monterey, California, Dec. 2000, 199 pages.
Bar, A., et al., "Adaptive Microcomputer Control of an Artificial Knee in Level Walking", J. Biomed Eng., 1983, vol. 5, pp. 145-150.
Baten, C.T., et al., "Inertial Sensing in Ambulatory Back Load Estimation", 18th Annual International Conference of the IEEE Engineering in Medicine and Biology Society, Amsterdam 1996, 2.6.3: Biomechanics.—Instrumentation, pp. 497-498.
Blaya, J.A., "Force-Controllable Ankle Foot Orthosis (AFO) to Assist Drop Foot Gait", Feb. 2003 (believed to be catalogued on or after Jul. 8, 2003), 97 pages, Massachusetts Institute of Technology.
Blumentritt, S., et al.; "Design Principles, Biomedical Data and Clinical Experience with A Polycentric Knee Offering Controlled Stance Phase Knee Flexion: A Preliminary Report", 1997, Journal of Prosthetics and Orthotics, vol. 9, No. 1, pp. 1-18.
van den Bogert, A.J., et al., "A Method for Inverse Dynamic Analysis Using Accelerometry", J. Biomechanics, 1996, 29(7):949-954.
Bortz, J.E., "A New Mathematical Formulation for Strapdown Inertial Navigation", IEEE Transactions on Aerospace and Electronic Systems, vol. AES-7, No. 1, Jan. 1971, pp. 61-66.
Bouten, C.V., et al., "A Triaxial Accelerometer and Portable Data Processing Unit for the Assessment of Daily Physical Activity", IEEE Transactions on Biomedical Engineering, 44(3):136-147, Mar. 1997.
Bouten, C.V., et al., "Assessment of Energy Expenditure for Physical Activity Using a Triaxial Accelerometer", Official Journal of the American College of Sports Medicine, Aug. 1994, pp. 1516-1523.
Carlson, J.D., et al., "Smart Prosthetics Based on Magnetorheological Fluids", 8th Annual Symposium on Smart Structures and Materials, Newport Beach, CA, Mar. 2001, 9 pages
Carlson, J.D., "What makes a Good MR Fluid?", 8th International Conference on Electrorheological (ER) Fluids and Magnetorheological (MR) Suspensions, Nice, Jul. 9-13, 2001, 7 pages.
Copes/Bionic Ankle, The Most Significant Development in Ankle Prosthetics in Over a Half Century, 1985, 4 pages.
Crago, P.E., et al., "New Control Strategies for Neuroprosthetic Systems", Journal of Rehabilitation Resarch and Development, Apr. 1996, 33(2):158-172.
Dai, R, et al., "Application of Tilt Sensors in Functional Electrical Stimulation", IEEE Transactions on Rehabilitation Engineering, Jun. 1996; 4(2):63-72.
Fisekovic, N., et al., "New Controller for Functional Electrical Stimulation Systems", Medical Engineering & Physcis, 2001, vol. 23, pp. 391-399.
Foerster, F., et al., "Detection of Posture and Motion by Accelerometry: A Validation Study in Ambulatory Monitoring", Computers in Human Behavior, 1999, vol. 15, pp. 571-583.
Foxlin, E., et al., "Miniature 6-DOF Inertial System for Tracking HMDs", SPIE vol. 3362, Helmet and Head-Mounted Displays III, AeroSense 98, Orlando, FL, Apr. 13-14, 1998, 15 pages.
Fujita, K., et al., "Joint Angle Control with Command Filter for Human Ankle Movement Using Functional Electrical Stimulation", Proceedings of the 9th Annual Conference of the IEEE Engineering in Medicine and Biology Society, The Boston Park Plaza Hotel, Boston, MA, Nov. 13-16, 1987, 4 pages.
Gelat, T., et al., "Adaptation of the gait initiation process for stepping on to a new level using a single step", Exp Brain Res, 2000, 133-538-546, Jun. 21, 2000, 9 pages.
Graps, A., "An Introduction to Wavelets", IEEE Computational Science & Engineering, Summer 1995, pp. 50-61.
Grimes, D.L., "An Active Multi-Mode Above-Knee Prosthesis Controller", Massachusetts Institute of Technology, Jun. 1979, 158 pages.
Grönqvist, R., et al., "Human-centered approaches in slipperiness measurement", National Institute of Health, Ergonomics, Oct. 20, 2001, vol. 44, Issue 13, pp. 1167-1199 (32 pages).

(56) References Cited

OTHER PUBLICATIONS

Hanafusa, H., et al., "A Robot Hand with Elastic Fingers and Its Application to Assembly Process," Robot Motion, Brady et al., MIT Press, Cambridge, MA, 1982, pp. 337-359.
Hanson, J.P., et al., "Predicting slips and falls considering required and available friction", Ergonomics, 1999, vol. 42, No. 12, pp. 1619-1633 (15 pages).
Hashimoto et al., "An instrumented compliant wrist using a parallel mechanism," Proceedings of the 1992 Japan/USA Symposium on Flexible Automation, vol. 1, pp. 741-744, ASME, 1992.
Hayes, W.C., et al., "Leg Motion Analysis During Gait by Multiaxial Accelerometry: Theoretical Foundations and Preliminary Validations", Journal of Biomechanical Engineering, Aug. 1983, vol. 105, pp. 283-289.
Herr, H., et al., "User-adaptive control of a magnetorheological prosthetic knee", Industrial Robot: An International Journal, 2003, vol. 30, No. 1, pp. 42-55.
Herr, H., et al., "Patient-Adaptive Prosthetic and Orthotic Leg Systems", 12th Nordic Baltic Conference on Biomedical Engineering and Medical Physics, Proceedings of the International Federation for Medical & Biological Engineering, 2002, 4 pages.
Herr, H., "Experiencing a New Frontier in Biomedical Technology", Harvard-MIT Division of Health Science and Technology presents Experiencing the Frontiers of Biomedical Technology, Mar. 10-11, 2003, 1 page.
Heyn, A., et al., "The Kinematics of the Swing Phase Obtained From Accelerometer and Gyroscope Measurements", 18th Annual International Conference of the IEEE Engineering in Medicine and Biology Society, Amsterdam 1996, 2.6.1:Locomotion, pp. 463-464.
Hill, S.W., et al., "Altered kinetic strategy for the control of swing limb elevation over obstacles in unilateral below-knee amputee gait", Journal of Biomechanics, 1999, vol. 32, pp. 545-549 (5 pages).
Howard, R.D., "Joint and Actuator Design for Enhanced Stability in Robotic Force Control," Ph.D. thesis, Massachusetts Institute of Technology, Dept. Of Aeronautics and Astronautics, Sep. 1990, 219 pages.
Jonić, S., et al., "Three Machine Learning Techniques for Automatic Determination of Rules to Control Locomotion", IEEE Transactions on Biomedical Engineering, Mar. 1999, 46(3):300-310.
Kidder, S.M., et al., "A System for the Analysis of Foot and Ankle Kinematics During Gait", IEEE Transactions on Rehabilitation Engineering, Mar. 1996, vol. 4, No. 1, pp. 25-32.
Kirkwood, C.A., et al., "Automatic Detection of Gait Events: A Case Study Using Inductive Learning Techniques", J. Biomed. Eng., Nov. 1989, vol. 11, pp. 511-516.
Kirsner, S., "A Step in the Right Direction Biomedical Horizons Expanding," Globe Newspaper Company, Boston Globe, MA, Mar. 17, 2003, 4 pages.
van der Kooij, H., et al., "A Multisensory Integration Model of Human Stance Control", Biol. Cybern., 1999, vol. 80, pp. 299-308.
Kostov, A., et al., "Machine Learning in Control of Functional Electrical Stimulation Systems for Locomotion", IEEE Transactions on Biomedical Engineering, Jun. 1995, 42(6):541-551.
Kuster, M., et al., "Kinematic and kinetic comparison of downhill and level walking", Clinical Biomechanics, 1995, vol. 10, No. 2, pp. 79-84 (6 pages).
LaFortune, M.A., "Three-Dimensional Acceleration of the Tibia During Walking and Running", J. Biomechanics, 1991, vol. 24, No. 10, pp. 877-886.
Lee, S.W., et al., "Activity and Location Recognition Using Wearable Sensors", Pervasive Computing, IEEE, 2002, pp. 24-32.
Light, L.H., et al., "Skeletal Transients on Heel Strike in Normal Walking with Different Footwear", J. Biomechanics, 1980, vol. 13, pp. 477-480.
Luinge, H.J., "Inertial Sensing of Movement", Doctoral Thesis, Twente University Press, Enschede, Netherlands, 2002, 80 pages.

Mayagoitia, R.E., et al., "Accelerometer and Rate Gyroscope Measurement of Kinematics: An Inexpensive Alternative to Optical Motion Analysis Systems", Journal of Biomechanics, 2002, vol. 35, pp. 537-542.
Moe-Nilssen, R., "A New Method for Evaluating Motor Control in Gait Under Real-Life Environmental Conditions", Clinical Biomechanics, 1998, vol. 13, pp. 320-327.
Morris, J.R.W., "Accelerometry—A Technique for the Measurement of Human Body Movements", J. Biomechanis, 1973, vol. 6, pp. 729-736.
Moseley, A.M., et al., "High- and low-ankle flexibility and motor task performance", Gait and Posture, 2003, vol. 18, pp. 73-80 (8 pages).
Nadeau, S., et al., "Frontal and sagittal plane analyses of the stair climbing task in healthy adults aged over 40 years: what are the challenges compared to level walking?", Clinical Biomechanics, 2003, vol. 18, pp. 950-959 (10 pages).
Nakagawa, A., "Intelligent Knee Mechanism and the Possibility to Apply the Principle to the Other Joints", Proceedings of the 20th Annual International Conference of the IEEE Engineering in Medicine and Biology Society, Dec. 1998, vol. 20, No. 5, pp. 2282-2287.
Otto Bock Orthopädische Industrie GMBH & Co., C-Leg Fitting Statistics (Abstract), Mar. 2000, 4 pages.
Otto Bock Orthopädische Industrie, C-LEG A new dimension in amputee mobility, Otto Bock Data Sheet, 1997, 4 pages.
Otto Bock Orthopädische Industrie, Quality for Life, The Electronic C-Leg compact Leg Prosthesis System, Instructions for Use, 2002, 28 pages.
Otto Bock Orthopadische Industrie, The Electronic C-Leg Knee Joint System, Instructions for Use, 2002, available at http://www.ottobockus.com/products/lower_limb_prosthetics/c-leg_instructions.pdg, 32 pages (printed Jul. 20, 2006).
Petrofsky, J.S., et. al., "Feedback Control System for Walking in Man", Comput. Biol. Med., 1984, vol. 14, No. 2, pp. 135-149.
Pfeffer, L.E., et al., "Experiments with a Dual-Armed, Cooperative, Flexible-Drivetrain Robot System", Proc. 1993 IEEE Int. Conf. on Robotics & Automation, May 5, 1993, vol. 3, pp. 601-608.
Popović, D. et al., "Optimal control for an Above-Knee Prosthesis With Two Degrees of Freedom", J. Biomechanics, 1995, vol. 28, No. 1, pp. 89-98.
Popovic, D., et al., "Control Aspects of Active Above-Knee Prosthesis", International Journal of Man-Machine Studies, Dec. 1991, vol. 35, pp. 751-767.
Powers, C.M., et al., "Stair ambulation in persons with transtibial amputation: An analysis of the Seattle LightFoot™", Journal of Rehabilitation Research and Development, Jan. 1997, vol. 34, No. 1, pp. 9-18 (10 pages).
Rao, S.S., et al., "Segment Velocities in Normal and Transtibial Amputees: Prosthetic Design Implications", IEEE Transactions on Rehabilitation Engineering, Jun. 1998, vol. 6, No. 2, pp. 219-226 (8 pages).
Redfern, M.S., et al., "Biomechanics of descending ramps", Gait and Posture, 1997, vol. 6, pp. 119-125 (7 pages).
Reiner, R., et al., "Stair ascent and descent at different inclinations", Gait and Posture, 2002, vol. 15, pp. 32-44 (13 pages).
Rietman, J. S., et al., "Gait Analysis in Prosthetics: Opinions, Ideas, and Conclusions", Prosthetics and Orthotics International, 2002, vol. 26, pp. 50-57 (8 pages).
Robinson, D.W. et al., "Series Elastic Actuator Development for a Biomimetic Walking Robot", MIT Leg Laboratory, Cambridge, MA, 1999, 8 pages.
Robinson, D.W., "Design and Analysis of Series Elasticity in Closed-Loop Actuator Force Control", MIT Department of Mechanical Engineering, Jun. 2000, 123 pages.
Schmalz, T., et al., "Energy Efficiency of Trans-Femoral Amputees Walking on Computer-Controlled Prosthetic Knee Joint "C-Leg"", International Society for Prosthetics and Orthotics: Conference book IXth World Congress ISPO, Amsterdam, Jun. 1998, 4 pages.
Sekine, M., et al., "Classification of Waist-Acceleration Signals in a Continuous Walking Record", Medical Engineering & Physics, 2000, vol. 22, pp. 285-291.
Sin, S. W., et al., "Significance of Non-Level Walking on Transtibial Prosthesis Fitting with Particular Reference to the Effects of Ante-

(56) References Cited

OTHER PUBLICATIONS rior-Posterior Alignment", Journal of Rehabilitation Research and Development, Jan./Feb. 2001, vol. 38, No. 1, pp. 1-6.

Smidt, G.L., et al., "An Automated Accelerometry System for Gait Analysis", J. Biomechanics. 1977, vol. 10, pp. 367-375.

State-of-the-Art Prosthetic Leg Incorporates Magneto-Rheological Technology, Medical Product Manufacturing News, p. 42, Nov. 2000.

Suga, T, et al., "Newly designed computer controlled knee-ankle-foot orthosis (Intellegent Orthosis)", Prostetics and Orthotics International, 1998, vol. 22, pp. 230-239.

Sugano, S., et al., "Force Control of the Robot Finger Joint equipped with Mechanical Compliance Adjuster", Proceedings of the 1992 IEEE/RSJ International Conference on Intelligent Robots & Systems, Raleigh, NC, Jul. 7-10, 1992, pp. 2005-2013.

Thakkar, S., "Energy Economy Gait Analysis of an Autoadaptive Prosthetic Knee", Master's Thesis submitted to the Dept. of Electrical Engineering and Computer Science, MIT, Aug. 30, 2002, 58 pages.

Tomović, R., et al., "A Finite State Approach to the Synthesis of Bioengineering Control Systems", IEEE Transactions on Human Factors in Electronics, Jun. 1966, vol. HFE-7, No. 2, pp. 65-69.

Tong, K.Y., et al., "Virtual Artificial Sensor Technique for Functional Electrical Stimulation", Medical Engineering & Physics, 1998, vol. 20, pp. 458-468.

Tong, K., "A Practical Gait Analysis System Using Gyroscopes", Medical Engineering & Physics, Mar. 1999, vol. 21, pp. 87-94.

Townsend, M.A., et al., "Biomechanics and modeling of bipedal climbing and descending", Journal of Biomechanics, 1976, vol. 9, No. 4, pp. 227-239, XP008078405.

U.S. Appl. No. 60/371,974 to Martin, filed Apr. 12, 2002, 49 pages.

Van der Loos, H.F.M., et al., "ProVAR Assistive Robot System Architecture", Proceedings of the 1999 IEEE International Conference on Robotics & Automation, Detroit, Michigan, May 1999, pp. 741-46.

Veltink, P.H., et al., "The Feasibility of Posture and Movement Detection by Accelerometry", 15th Annual International Conference of the IEEE Engineering in Medicine and Biology Society, Oct. 28-31, 1993, San Diego, CA, 1230-1231.

Veltink, P.H., et al., "Detection of Static and Dynamic Activities Using Uniaxial Accelerometers", IEEE Transactions on Rehabilitation Engineering, Dec. 1996, vol. 4, No. 4, pp. 375-385.

Wilkenfeld, A., et al., "An Auto-Adaptive External Knee Prosthesis", Artificial Intelligence Laboratory, MIT, Cambridge, Massachusetts, Sep. 2000, 3 pages.

Wilkenfeld, A., "Biologically inspired autoadaptive control of a knee prosthesis", Dissertation Abstract, MIT, Cambridge, Massachusetts, Sep. 2000, 1 page.

Willemsen, A.T.M., et al., "Real-Time Gait Assessment Utilizing a New Way of Accelerometry", J. Biomechanics, 1990, vol. 23, No. 8, pp. 859-863.

Willemsen, A.T.M., et al., Automatic Stance-Swing Phase Detection from Accelerometer Data for Peroneal Nerve Stimulation, IEEE Transactions on Biomedical Engineering, Dec. 1990, vol. 37, No. 12, pp. 1201-1208.

Williamson, M.M., "Series Elastic Actuators", Massachusetts Institute of Technology Artificial Intelligence Laboratory, A.I. Technical Report No. 1524, Jan. 1995, pp. 1-83.

Woodward, M.I., et al., "Skeletal Accelerations Measured During Different Exercises", Proceedings of the Institution of Mechanical Engineers, Part H: Journal of Engineering Medicine, 1993, 207:79, DOi: 10.1243/PIME_PROC_1993_207_274_02, 8 pages.

Wu, G., et al., "The Study of Kinematic Transients in Locomotion Using the Integrated Kinematic Sensor", IEEE Transactions on Rehabilitation Engineering, Sep. 1996, vol. 4, No. 3, pp. 193-200.

Au et al., "An EMG-Position Controlled System for an Active Ankle-Foot Prosthesis: An Initial Experimental Study," Proceedings of the 2005 IEEE 9th International Conference on Rehabilitation Robotics, Chicago, IL, Jun. 28-Jul. 1, 2005, pp. 375-379.

DIGINFO TV, "Powered Prosthetic Thigh and Leg", uploaded Nov. 7, 2008 http://www.youtube.com/watch?v=lqjtTzNEd54 &feature=youtu.be%3E [Screenshots retrieved Oct. 23, 2014 in 9 pages].

"Extension Spring Design Theory, Spring Rate of Extension Springs," http://web.archive.org/web/20131209120508/http://springipedia.com/extension-design-theory.asp as archived Dec. 9, 2013 in 1 page.

Lelas et al., "Hydraulic Versus Magnetorheological-Based Electronic Knee Prostheses: A Clinical Comparison," Massachusetts, 2004, pp. 1-16.

Martens, W.L.J.; "Exploring Information Content and Some Application of Body Mounted Piezo-Resistive Accelerometers," In P.H. Veltink, & R.C. van Lummel (Eds.), Dynamic analysis using body fixed sensors, Second World Congress of Biomechanics, Amsterdam, 1994, pp. 9-12. Asserted by iWalk in Civil Action No. 12-CV-11061 FDS to constitute prior art to U.S. Pat. Nos. 7,431,737 and 7,896,927. Applicant requests that the Examiner to consider this reference as qualifying as prior art to the present application, but reserves the right to challenge the reference's prior art status at a later date.

Murray et al., "Walking Patterns of Normal Men," The Journal of Bone and Joint Surgery, vol. 46-A, No. 2, Mar. 1964.

Perry, Jacquelin MD, "Gait Analysis:Normal and Pathological Function," Ch. 4, pp. 51-53, 85-87, 1992.

Perry, Jacquelin MD, "Gait Analysis:Normal and Pathological Function," Ch. 5, pp. 92-108, 1992.

\* cited by examiner

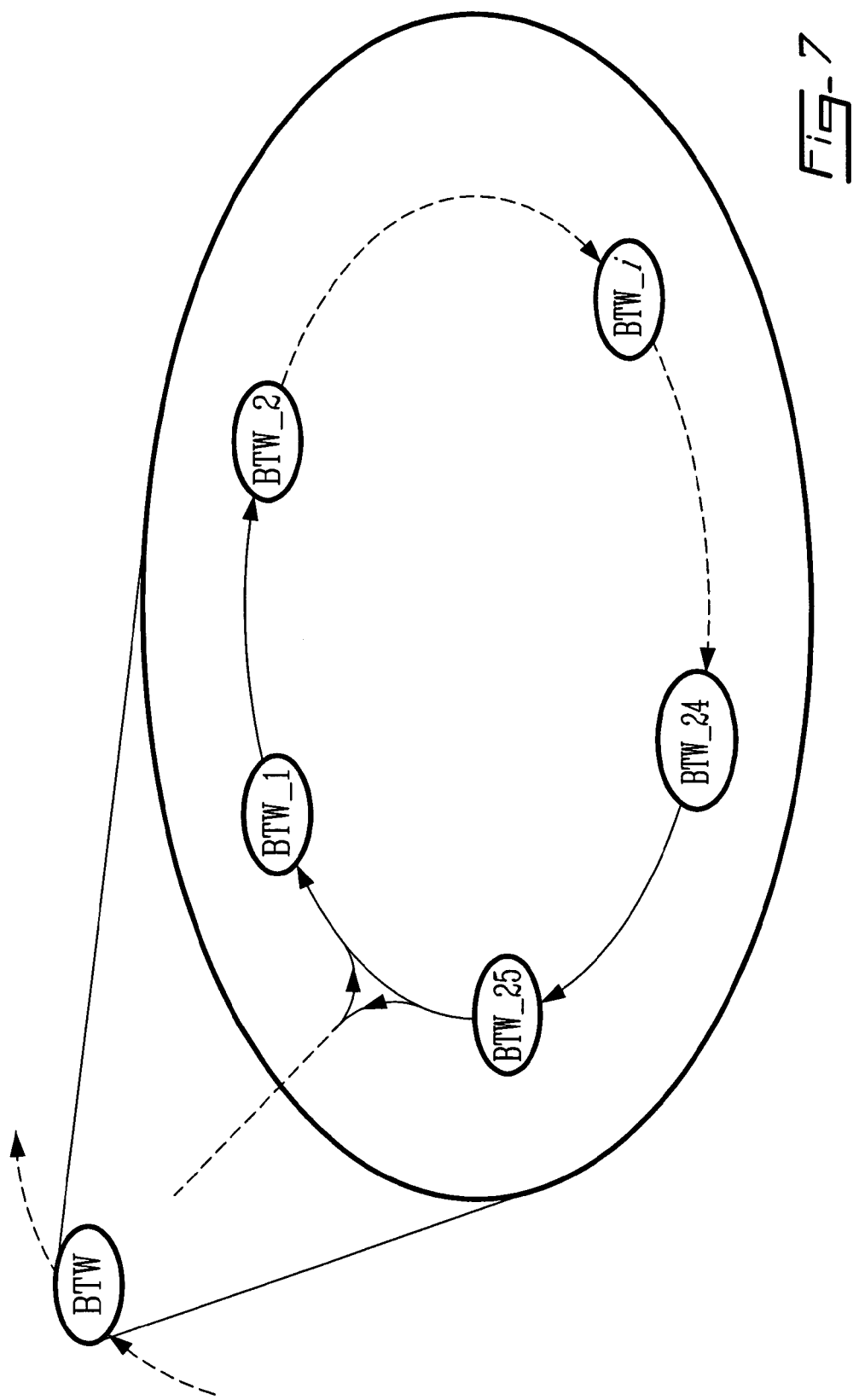

CONTROL DEVICE AND SYSTEM FOR CONTROLLING AN ACTUATED PROSTHESIS

CROSS-REFERENCE TO RELATED APPLICATIONS

The present application is a continuation of U.S. patent application Ser. No. 12/987,801 filed Jan. 10, 2011, entitled "CONTROL DEVICE AND SYSTEM FOR CONTROLLING AN ACTUATED PROSTHESIS," now abandoned, which is a continuation of U.S. patent application Ser. No. 11/270,684 filed Nov. 9, 2005, now issued as U.S. Pat. No. 7,867,284, entitled "CONTROL DEVICE AND SYSTEM FOR CONTROLLING AN ACTUATED PROSTHESIS," which is a divisional of U.S. patent application Ser. No. 10/600,725 filed Jun. 20, 2003, now issued as U.S. Pat. No. 7,147,667, which claims the benefit of U.S. provisional patent application Nos. 60/453,556 filed Mar. 11, 2003, 60/424,261 filed Nov. 6, 2002, and 60/405,281 filed Aug. 22, 2002, all of which are hereby incorporated by reference in their entirety.

TECHNICAL FIELD

The present invention relates to a control system and a method for controlling an actuated prosthesis. This invention is particularly well adapted for controlling an actuated leg prosthesis for above-knee amputees.

BACKGROUND

As is well known to control engineers, the automation of complex mechanical systems is not something easy to achieve. Among such systems, conventional powered artificial limbs, or myoelectric prostheses, as they are more commonly referred to, are notorious for having control problems. These conventional prostheses are equipped with basic controllers that artificially mobilize the joints without any interaction from the amputee and are only capable of generating basic motions. Such basic controllers do not take into consideration the dynamic conditions of the working environment, regardless of the fact that the prosthesis is required to generate appropriate control within a practical application. They are generally lacking in predictive control strategies necessary to anticipate the artificial limb's response as well as lacking in adaptive regulation enabling the adjustment of the control parameters to the dynamics of the prosthesis. Because human limb mobility is a complex process including voluntary, reflex and random events at the same time, conventional myoelectric prostheses do not have the capability to interact simultaneously with the human body and the external environment in order to have minimal appropriate functioning.

For example, in the case of artificial leg prostheses for above-knee amputees, the complexity of human locomotion resulted in that the technical improvements of conventional leg prostheses have until now been focused on passive mechanisms. This proved to be truly detrimental to the integration of motorized leg prostheses onto the human body. According to amputees, specific conditions of use of conventional leg prostheses, such as repetitive movements and continuous loading, typically entail problems such as increases in metabolic energy expenditures, increases of socket pressure, limitations of locomotion speeds, discrepancies in the locomotion movements, disruptions of postural balance, disruptions of the pelvis-spinal column alignment, and increases in the use of postural clinical rehabilitation programs.

The major problem remains that the energy used during mobility mainly stems from the user because conventional leg prostheses are not equipped with servomechanisms that enable self-propulsion. This energy compensation has considerable short and long-term negative effects resulting from the daily use of such prostheses. Accordingly, the dynamic role played by the stump during locomotion renders impossible the prolonged wearing of the prostheses as it may create, among other things, several skin problems such as folliculitis, contact dermatitis, edema, cysts, skin shearing, scarring and ulcers. Although these skin problems may be partially alleviated by using a silicone sheath, a complete suction socket, or powder, skin problems remain one of the major preoccupations today.

As well, the passive nature of the conventional leg prostheses typically leads to movement instability, disrupted movement synchronism and reduced speed of locomotion. Recent developments in the field of energy-saving prosthetic components have partially contributed to improve energy transfer between the amputee and the prosthesis. Nevertheless, the problem of energy expenditure is still not fully resolved and remains the major concern.

Considering this background, it clearly appears that there was a need to develop an improved control system and a new method for controlling an actuated prosthesis in order to fulfill the needs of amputees, in particular those of above-knee amputees.

SUMMARY

In accordance with one aspect of the present invention, there is provided a method for determining a portion of locomotion and a phase of locomotion portion in view of controlling an actuated prosthesis in real time, the method comprising:

providing a plurality of main artificial proprioceptors;

receiving a data signal from each of the main artificial proprioceptors;

obtaining a first and a second derivative signal for each data signal;

obtaining a third derivative signal for at least one of the data signals;

using a set of a first state machines to select one state among a plurality of possible states for each main artificial proprioceptor with the corresponding data and derivative signals;

generating the phase of locomotion portion using the states of the main artificial proprioceptors; and using a second state machine to select the portion of locomotion among a plurality of possible portions of locomotion using events associated to the data signals.

In accordance with another aspect of the present invention, there is provided a method for controlling an actuated prosthesis in real time, the method comprising:

providing a plurality of main artificial proprioceptors;

receiving a data signal from each of the main artificial proprioceptors;

obtaining a first and a second derivative signal for each data signal;

obtaining a third derivative signal for at least one of the data signals;

using a set of first state machines to select one state among a plurality of possible states for each main artificial proprioceptor with the corresponding data and derivative signals;

generating the phase of locomotion portion using the states of the main artificial proprioceptors;

using a second state machine to select the portion of locomotion among a plurality of possible portions of locomotion using events associated to the data signals;

calculating a locomotion speed value;

determining coefficient values from a lookup table using at least the phase of locomotion portion, the portion of locomotion and the locomotion speed value;

calculating at least one dynamic parameter value of the actuated prosthesis using the coefficient values from the lookup table; and converting the dynamic parameter value into an output signal to control the actuated prosthesis.

In accordance with a further aspect of the present invention, there is provided a device for determining a portion of locomotion and a phase of locomotion portion in view of controlling an actuated prosthesis in real time using a plurality of main artificial proprioceptors, the device comprising:

a data signal input for each of the main artificial proprioceptors;

means for obtaining a first and a second derivative signal for each data signal;

means for obtaining a third derivative signal for at least one of the data signals;

a set of first state machines, the first state machines being used to select one state among a plurality of possible states for each main artificial proprioceptor with the corresponding data and derivative signals;

means for generating the phase of locomotion portion using the states of the main artificial proprioceptors; and a second state machine, the second state means being used to select the portion of locomotion among a plurality of possible portions of locomotion using events associated to the data signals.

In accordance with a further aspect of the present invention, there is provided a control system for controlling an actuated prosthesis in real time, the system comprising:

a plurality of main artificial proprioceptors;

means for obtaining a first and a second derivative signal for each data signal;

means for obtaining a third derivative signal for at least one of the data signals;

a set of first state machines, the first state machines being used to select one state among a plurality of possible states for each main artificial proprioceptor with the corresponding data and derivative signals;

means for generating the phase of locomotion portion using the states of the main artificial proprioceptors;

a second state machine, the second state machine being used to select the portion of locomotion among a plurality of possible portions of locomotion using events associated to data signals;

means for calculating a locomotion speed value;

means for storing a lookup table comprising coefficient values with reference to at least phases of locomotion, portions of locomotion and locomotion speed values;

means for determining actual coefficient values from the lookup table using at least the phase of locomotion portion, the portion of locomotion and the locomotion speed value;

means for calculating at least one dynamic parameter value of the actuated prosthesis using the coefficient values from the lookup table; and means for converting the dynamic parameter value into an output signal to control the actuated prosthesis.

These and other aspects of the present invention are described in or apparent from the following detailed description, which description is made in conjunction with the accompanying figures.

BRIEF DESCRIPTION OF THE FIGURES

FIG. 7 is an example of the phases of locomotion portion within one portion of locomotion (BTW) in the state machine diagram shown in FIG. 6;

ACRONYMS

Figure 1:
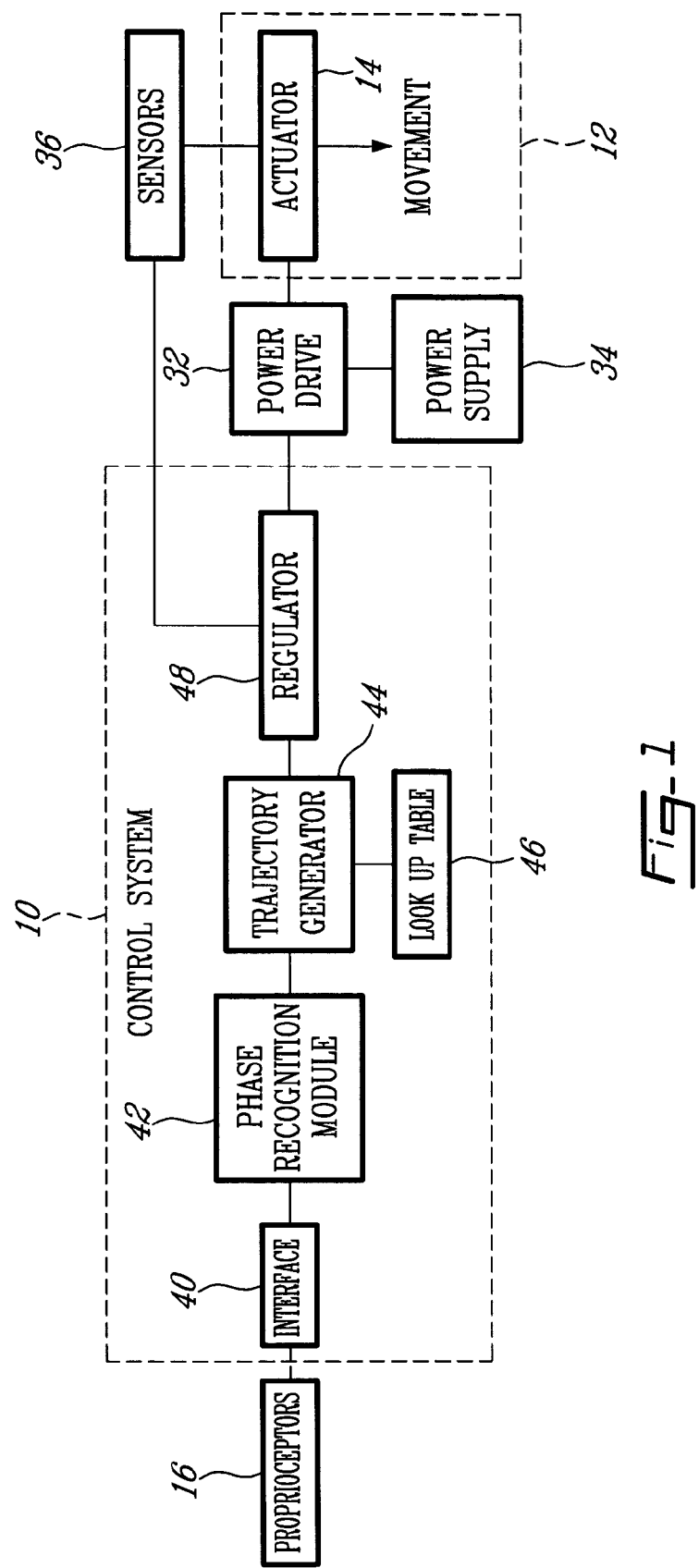
FIG. 1 is a block diagram showing the control system in accordance with a preferred embodiment of the present invention.

The detailed description and figures refer to the following technical acronyms:

A/D Analog/Digital
BDW "Downward Inclined Walking—Beginning path" portion of locomotion
BGD "Going Down Stairs—Beginning path" portion of locomotion
BGU "Going Up Stairs—Beginning path portion of locomotion
BTW "Linear Walking—Beginning path" portion of locomotion
BTW_SWING Detection of typical walking $g_{r\_leg}$ during leg swing
BUW "Upward Inclined Walking—Beginning path" portion of locomotion
CDW "Downward Inclined Walking—Cyclical path" portion of locomotion
CGD "Going Down Stairs—Cyclical path" portion of locomotion
CGU "Going Up Stairs—Cyclical path" portion of locomotion
CTW "Linear Walking—Cyclical path" portion of locomotion
CUW "Upward Inclined Walking—Cyclical path" portion of locomotion
ECW "Curve Walking Path" portion of locomotion
EDW "Downward Inclined Walking—Ending path" portion of locomotion
EGD "Going Down Stairs—Ending path" portion of locomotion
EGU "Going Up Stairs—Ending path" portion of locomotion
ETW "Linear Walking—Ending path" portion of locomotion
EUW "Upward Inclined Walking—Ending path" portion of locomotion
FR_BIN$_x$ Detection of a positive $f_{rx}$
FRfst_BIN$_x$ Detection of positive first differentiation of $f_{rx}$
FRsec_BIN$_x$ Detection of positive second differentiation of $f_{rx}$
FRtrd_BIN$_x$ Detection of positive third differentiation of $f_{rx}$
FR_HIGH$_x$ Detection of $f_{rx}$ level above the STA envelope
FR_LOW$_x$ Detection of $f_{rx}$ level between the zero envelope and the STA envelope
FSR Force Sensing Resistor
GR_POS$_y$ Detection of a positive $g_{ry}$
MIN_SIT Detection of a minimum time in portion SIT
MP Metatarsophalangeal
PID Proportional-Integral-Differential
PKA_SDW Sit down knee angle
PKA_ETW End walking knee angle
PKA_STA Stance knee angle
PKA_SIT Sit down knee angle
PKA_SUP_RAMP Standing up knee angle
PPMV Plantar Pressure Maximal Variation
PPS Plantar Pressure Sensor
PRM Phase Recognition Module
REG Regulator
RF Radio Frequency
SDW "Sitting down" portion of locomotion
SIT "Sitting" portion of locomotion
STA "Stance of fee" portion of locomotion
STA_BIN Detection of a static evolution of all $F_{rx}$
STATIC_GR$_y$ Detection of $g_{ry}$ level below the zero angular speed envelope and the zero acceleration envelope
sum$_a$ Localized plantar pressure signal of left foot
sum$_b$ Localized plantar pressure signal of right foot
sum$_c$ Localized plantar pressure signal of both calcaneus
sum$_d$ Localized plantar pressure signal of both MP
sum$_e$ Localized plantar pressure signal of both feet
SUM_BIN$_y$ Non-Zero of sum$_y$
SUP "Standing Up" portion of locomotion
SVD Singular Values Decomposition
SWING$_y$ Detection of a swing prior to a foot strike
TG Trajectory Generator
XHLSB Heel Loading State Bottom (X=Left (L) or Right))
XHLSM Heel Loading State Middle (X=Left (L) or Right))
XHLST Heel Loading State Top (X=Left (L) or Right))
XHSTA Heel STAtic state (X=Left (L) or Right))
XHUSB Heel Unloading State Bottom (X=Left (L) or Right))
XHUST Heel Unloading State Top (X=Left (L) or Right))
XHZVS Heel Zero Value State (X=Left (L) or Right))
XMLSM MP Loading State Middle (X=Left (L) or Right))
XMLST MP Loading State Top (X=Left (L) or Right))
XMSTA MP STAtic state (X=Left (L) or Right))
XMUSB MP Unloading State Bottom (X=Left (L) or Right))
XMUST MP Unloading State Top (X=Left (L) or Right))
XMZVS MP Zero Value State (X=Left (L) or Right))
ZV_FRfst$_x$ Threshold to consider the first differentiation of $f_{rx}$ to be positive
ZV_FRsec$_x$ Threshold to consider the second differentiation of $f_{rx}$ to be positive
ZV_FRtrd$_x$ Threshold to consider the third differentiation of $f_{rx}$ to be positive
ZV_FR$_x$ Threshold to consider $f_{rx}$ to be positive
ZV_SUMfst Threshold to consider the absolute value of the 1st diff. of sum$_y$ to be positive
ZV_SUMsec Threshold to consider the absolute value of the 2nd diff. of sum$_y$ to be positive

DETAILED DESCRIPTION

The appended figures show a control system (10) in accordance with the preferred embodiment of the present invention. It should be understood that the present invention is not limited to the illustrated implementation since various changes and modifications may be effected herein without departing from the scope of the appended claims.

FIG. 1 shows the control system (10) being combined with an autonomous actuated prosthesis for amputees. It is particularly well adapted for use with an actuated leg prosthesis for above-knee amputees, such as the prostheses (12) shown in FIGS. 2 and 3. Unlike conventional prostheses, these autonomous actuated prostheses (12) are designed to supply the mechanical energy necessary to move them by themselves. The purpose of the control system (10) is to provide the required signals allowing to control an actuator (14). To do so, the control system (10) is interfaced with the amputee using artificial proprioceptors (16) to ensure proper coordination between the amputee and the movements of the actuated prosthesis (12). The set of artificial proprioceptors (16) captures information, in real time, about the dynamics of the amputee's movement and provides that information to the control system (10). The control system (10) is then used to determine the joint trajectories and the required force or torque that must be applied by the actuator (14) in order to provide coordinated movements.

Figure 2:
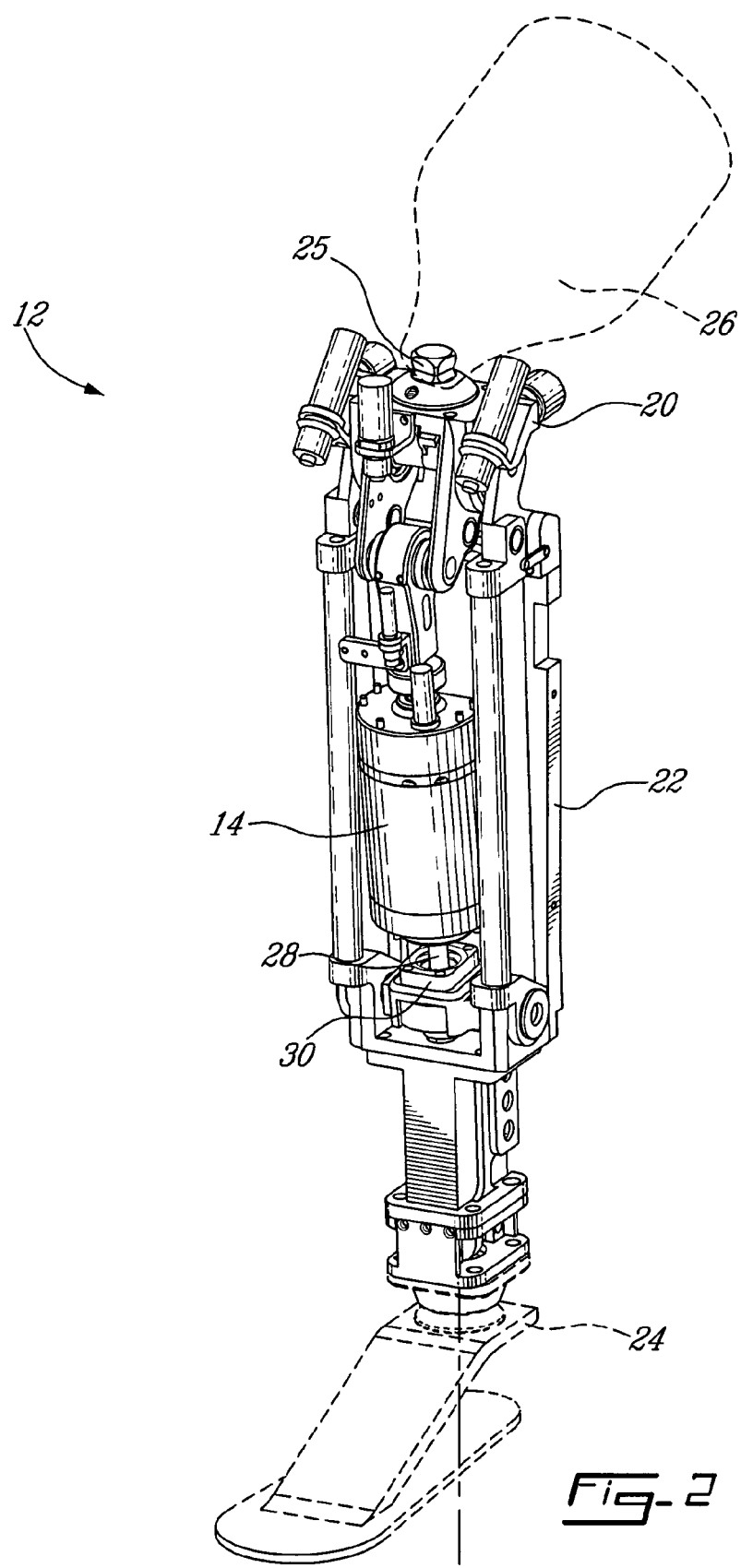
FIG. 2 is a perspective view of an example of an actuated prosthesis with a front actuator configuration.

FIG. 2 shows an example of an actuated leg prosthesis (12) for an above-knee amputee. This prosthesis (12) is powered by a linear actuator (14). The actuator (14) moves a knee member (20) with reference to a trans-tibial member (22), both of which are pivotally connected using a first pivot axis. More sophisticated models may be equipped with a more complex pivot or more than one pivot at that level.

An artificial foot (24) is provided under a bottom end of the trans-tibial member (22). The knee member (20) comprises a connector (25) to which a socket (26) can be attached. The socket (26) is used to hold the sump of the amputee. The design of the knee member (20) is such that the actuator (14) has an upper end connected to another pivot on the knee member (20). The bottom end of the actuator (14) is then connected to a third pivot at the bottom end of the trans-tibial member (22). In use, the actuator (14) is operated by activating an electrical motor therein. This rotates, in one direction or another, a screw (28). The screw (28) is then moved in or out with reference to a follower (30), thereby changing the relative angular position between the two movable parts, namely the knee member (20) and the trans-tibial member (22).

Figure 3:
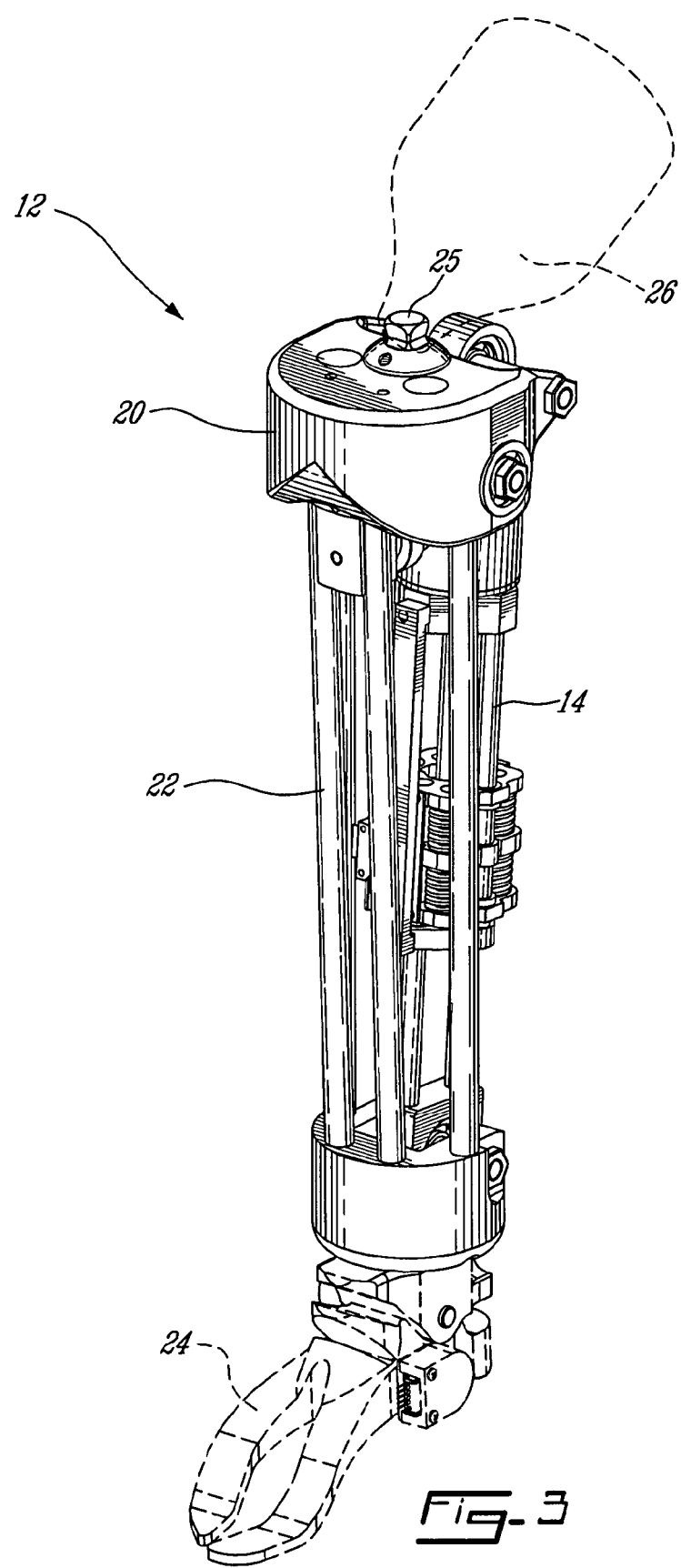
FIG. 3 is a perspective view of an example of an actuated prosthesis with a rear actuator configuration.

FIG. 3 shows an actuated leg prosthesis (12) in accordance to a rear actuator configuration. This embodiment is essentially similar to that of FIG. 2 and is illustrated with a different model of actuator (14).

It should be noted that the present invention is not limited to the mechanical configurations illustrated in FIGS. 2 and 3. The control system (10) may be used with a leg prosthesis having more than one joint. For instance, it can be used with a prosthesis having an ankle joint, a metatarsophalangeal joint or a hip joint in addition to a knee joint. Moreover, instead of a conventional socket a osseo-integrated devices could also be used, ensuring a direct attachment between the mechanical component of the prosthesis and the amputee skeleton. Other kinds of prostheses may be used as well.

Referring back to FIG. 1, the information provided by the artificial proprioceptors (16) are used by the control system (10) to generate an output signal. These output signals are preferably sent to the actuator (14) via a power drive (32) which is itself connected to a power supply (34), for instance a battery, in order to create the movement. The power drive (32) is used to control the amount of power being provided to the actuator (14). Since the actuator (14) usually includes an electrical motor, the power drive (32) generally supplies electrical power to the actuator (14) to create the movement.

Preferably, feedback signals are received from sensors (36) provided on the prosthesis (12). In the case of an actuated leg prosthesis (12) such as the one illustrated in FIGS. 2 and 3, these feedback signals may-indicate the relative position measured between two movable parts and the torque between them. This option allows the control system (10) to adequately adjust the output signal. Other types of physical parameters may be monitored as well.

The control system (10) shown in FIG. 1 comprises an interface (40) through which data signals coming from the artificial proprioceptors (16) are received. They may be received either from an appropriate wiring or from a wireless transmission. In the case of actuated leg prostheses for above-knee amputees, data signals from the artificial proprioceptors (16) provided on a healthy leg are advantageously sent through the wireless transmission using an appropriate RF module. For example, a simple off-the-shelf RF module with a dedicated specific frequency, such as 916 MHz, may be used. For a more robust implementation though, the use of a RF module with a spread spectrum or frequency hopper is preferable. Of course, other configurations may be used as well, such as a separate A/D converter, different resolution or sampling values and various combinations of communication link technologies such as wired, wireless, optical, etc.

The control system (10) further comprises a part called "Phase Recognition Module" or PRM (42). The PRM (42) is a very important part of the control system (10) since it is used to determine two important parameters, namely the portion of locomotion and the phase of locomotion portion. These parameters are explained later in the text. The PRM (42) is connected to a Trajectory Generator, or TG (44), from which dynamic parameters required to control the actuated prosthesis (12) are calculated to create the output signal. A lookup table (6) is stored in a memory connected to the TG (44). Moreover, the control system (10) comprises a regulator (48) at which the feedback signals are received and the output signal can be adjusted.

Software residing on an electronic circuit board contains all the above mentioned algorithms enabling the control system (10) to provide the required signals allowing to control the actuator (14). More specifically, the software contains the following three modules: the Phase Recognition Module (PRM), the Trajectories Generator (TG) and the Regulator (REG). Of course, any number of auxiliary modules may be added.

The artificial proprioceptors (16) preferably comprise main artificial proprioceptors and auxiliary artificial proprioceptors. The main artificial proprioceptors are preferably localized plantar pressure sensors which measure the vertical plantar pressure of a specific underfoot area, while the auxiliary artificial proprioceptors are preferably a pair of gyroscopes which measure the angular speed of body segments of the lower extremities and a kinematic sensor which measures the angle of the prosthesis knee joint. The plantar pressure sensors are used under both feet, including the artificial foot. It could also be used under two artificial feet if required. One of the gyroscopes is located at the shank of the normal leg while the other is located on the upper portion of the prosthesis above the knee joint. As for the kinematic sensor, it is located at the prosthesis knee joint. Other examples of artificial proprioceptors (16) are neuro-sensors which measure the action potential of motor nerves, myoelectrical electrodes which measure the internal or the external myoelectrical activity of muscles, needle matrix implants which measure the cerebral activity of specific region of the cerebrum cortex such as motor cortex or any other region indirectly related to the somatic mobility of limbs or any internal or external kinematic and/or kinetic sensors which measure the position and the torque at any joints of the actuated prosthesis. Of course, depending on the application, additional types of sensors which provide information about various dynamics of human movement may be used.

Figure 4:
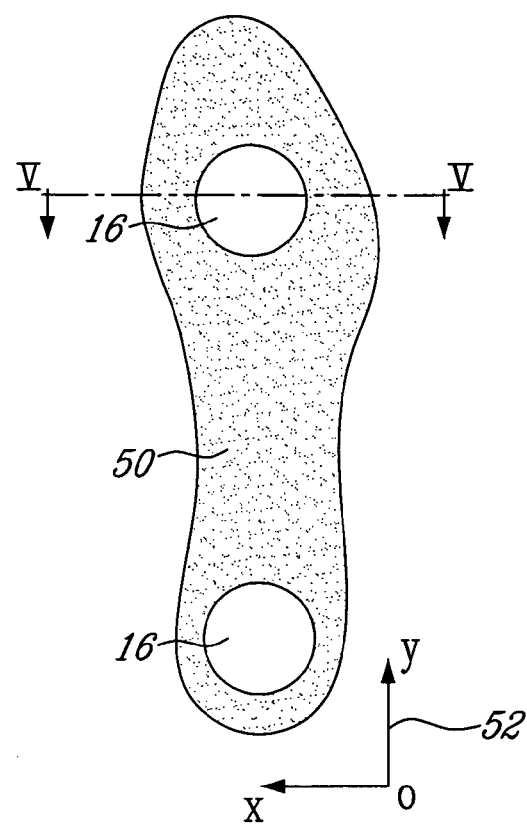
FIG. 4 is an upper schematic view of an insole provided with plantar pressure sensors.

FIG. 4 shows a right insole (10) provided with two plantar pressure sensors (16) positioned at strategic locations. Their size and position were defined in accordance with the stability and the richness (intensity) of the localized plantar pressure signals provided by certain underfoot areas during locomotion. Experimentation provided numerous data concerning the spatial distribution of foot pressures and more specifically on the Plantar Pressure Maximal Variation (PPMV) during locomotion. The PPMV, denoted $\Delta_{max} f_{r,ij}$, was defined as the maximum variation of the plantar pressure at a particular point (underfoot area of coordinate i,j) during locomotion. The X-Y axis (52) in FIG. 4 was used to determine the i,j coordinates of each underfoot area.

A PPMV of a given underfoot area of coordinates i,j during a given step denoted event x, is defined as stable, through a set of N walking steps, if the ratio of the absolute difference between this PPMV and the average PPMV over the set is inferior to a certain value representing the criteria of stability, thus:

$$\left(\frac{\left|\Delta_{max}f_{r,ij}\right|_x - \left|\frac{\sum_{n=0}^{N}\Delta_{max}f_{r,ij}\right|_n}{N}\right|}{\frac{\sum_{n=0}^{N}\left|\Delta_{max}f_{r,ij}\right|_n}{N}}\right) \cdot 100\% \leq (S\ \%) \qquad \text{Equation 1}$$

where $\Delta_{max}f_{r,ij}|_x$ is the PPMV localized at underfoot area of coordinates i,j during the event x, thus $$\Delta_{max}f_{r,ij}|_x = f_{r,ij}{}^{max}(k)|_{k\to 0\ to\ K} - f_{r,ij}{}^{min}(k)|_{k\to 0\ to\ K} \text{ for the event } x$$

K is the number of samples (frames),
N is the number of steps in the set,
S is the chosen criteria to define if a given PPMV is stable.

A PPMV of a given underfoot area of coordinates i,j during a given step denoted event x, is defined as rich in information, through a set of N walking steps, if the ratio between the PPMV and the average PPMV of the set is superior to certain value representing the criteria of richness thus:

$$\left|\Delta_{max}f_{r,ij}\right|_x \geq (R\ \%) \cdot \left(\left|\frac{\sum_{n=0}^{N}\Delta_{max}f_{r,ij}\right|_n}{N}\right)\right|_{max}{}^{i,j} \qquad \text{Equation 2}$$

where $\Delta_{max}f_{r,ij}|_x$ is the PPMV localized at underfoot area of coordinates i,j during the event x, thus $$\Delta_{max}f_{r,ij}|_x = f_{r,ij}{}^{max}(k)|_{k\to 0\ to\ K} - f_{r,ij}{}^{min}(k)|_{k\to 0\ to\ K} \text{ for the event } x$$

K is the number of samples (frames),
N is the number of steps in the set,
R is the chosen criteria to define if a given PPMV is rich in information.

It was found by experimentation that the size and the position of plantar pressure sensor are well defined when the criteria are set at 5% and 10% for the stability and the richness PPMV respectively. As a result, it was found that the calcaneus and the Metatarsophalangeal (MP) regions are two regions of the foot sole where the PPMV may be considered as providing a signal that is both stable and rich in information.

Figure 5:
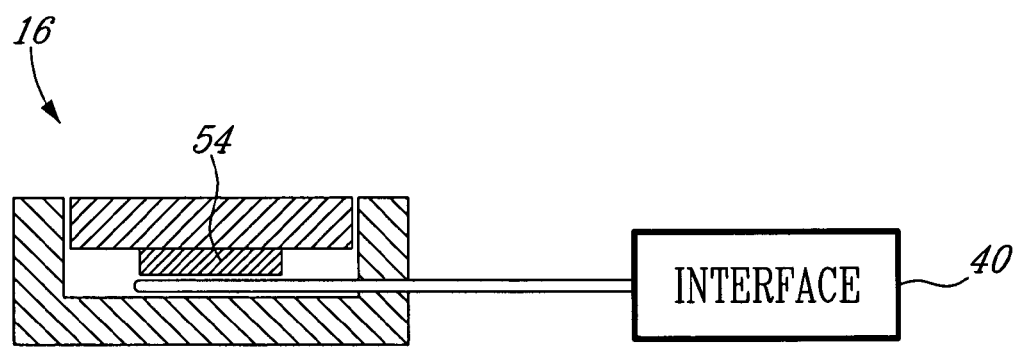
FIG. 5 is a cross sectional view of a sensor shown in FIG. 4.

In FIG. 4, the plantar pressure sensors (f6) are provided in a custom-made insole (10), preferably in the form of a standard orthopedic insole," that is modified to embed the two sensors (16) for the measurement of two localized plantar pressures. Each sensor (16), as shown in FIG. 5, is preferably composed of a thin Force-Sensing Resistor (FSR) polymer cell (54) directly connected to the interface (40) or indirectly using an intermediary system (not shown), for instance a wireless emitter. Mechanical adapters may be used if FSR cells of appropriate size are not available. The FSR cell (54) has a decreasing electrical resistance in response to an increasing force applied perpendicularly to the surface thereof. Each cell (54) outputs a time variable electrical signal for which the intensity is proportional to the total vertical plantar pressure over its surface area.

The normalized position of the pressure sensors and their size are shown in Table 1, where the length L and the width W are respectively the length and the width of the subject's foot. The coefficients in Table 1 have been obtained by experimentation. A typical diameter for the plantar pressure sensors (16) is between 20 and 30 mm.

TABLE 1

Normalized position and size of pressure sensors

| Area | Position (X, Y) | Size (diameter) |
|---|---|---|
| Calcaneus | (0.51 · W, 0.14 · L) | $0.29 \cdot \sqrt{L \cdot W}$ |
| MP | (0.7 · W, 0.76 · L) | $0.24 \cdot \sqrt{L \cdot W}$ |

In use, the PRM (42) ensures, in real-time, the recognition of the phase of locomotion portion and the portion of locomotion of an individual based on the information provided by the artificial proprioceptors (16). The PRM (42) is said to operate in real time, which means that the computations and other steps are performed continuously and with almost no delay.

In accordance with the present invention, it was found that data signals received from individual artificial proprioceptors (16) can provide enough information in order to control the actuator (14) of an actuated prosthesis (12). For instance, in the case of plantar pressure sensors, it has been noticed experimentally that the slope (first derivative), the sign of the concavity (second derivative) and the slope of concavity (third derivative) of the data signals received from plantar pressure sensors, and of combinations of those signals, give highly accurate and stable information on the human locomotion. The PRM (42) is then used to decompose of the human locomotion into three levels, namely the states of each artificial proprioceptor (16), the phase of locomotion portion and the portion of locomotion. This breakdown ensures the proper identification of the complete mobility dynamics of the lower extremities in order to model the human locomotion.

The actual states of each main artificial proprioceptor depict the first level of the locomotion breakdown. This level is defined as the evolution of the main artificial proprioceptors' sensors during the mobility of the lower extremities. Each sensor has its respective state identified from the combination of its data signal and its first three differential signals. For the main artificial proprioceptors of the preferred embodiment, which provide information about localized plantar pressures, it has been discovered experimentally that the localized plantar pressures signals located at the calcaneous and at the metatarsophalangeal (MP) regions may be grouped into seven and six states respectively.

For the sensors at the calcaneous regions, the states are preferably as follows:

| | |
|---|---|
| XHLSB | Heel Loading State Bottom (X = Left (L) or Right)) |
| XHLSM | Heel Loading State Middle (X = Left (L) or Right (R)) |
| XHLST | Heel Loading State Top (X = Left (L) or Right)) |
| XHSTA | Heel STAtic State (X = Left (L) or Right)) |
| XHUSB | Heel Unloading State Bottom (X = Left (L) or Right)) |
| XHUST | Heel Unloading State Top (X = Left (L) or Right)) |
| XHZVS | Heel Zero Value State (X = Left (L) or Right)) |

For the sensors at the MP regions, the states are preferably as follows:

| | |
|---|---|
| XMLSB | MP Loading State Bottom (X = Left (L) or Right)) |
| XMLST | MP Loading State Top (X = Left (L) or Right)) |
| XMSTA | MP STAtic State (X = Left (L) or Right)) |
| XMUSB | MP Unloading State Bottom (X = Left (L) or Right)) |
| XMUST | MP Unloading State Top (X = Left (L) or Right)) |
| XMZVS | MP Zero Value State (X = Left (L) or Right)) |

Identifying the states at each sensor allows to obtain the second level of the locomotion breakdown, referred to as the phase of locomotion portion. The phase of locomotion portion is defined as the progression of the subject's mobility within the third level of locomotion breakdown, namely the portion of locomotion. This third level of the locomotion breakdown defines the type of mobility the subject is currently in, such as, for example, standing, sitting or climbing up stairs. Each locomotion portion contains a set of sequential phases illustrating the progression of the subject's mobility within that locomotion portion. The phase sequence mapping for each locomotion portion has been identified by experimentation according to the evolution of the state of the localized plantar pressures throughout the portion.

The portions of locomotion are preferably as follows:

| | |
|---|---|
| BDW | "Downward Inclined Walking - Beginning path" |
| BGD | "Going Down Stairs - Beginning path" |
| BGU | "Going Up Stairs - Beginning path" |
| BTW | "Linear Walking - Beginning path" |
| BUW | "Upward Inclined Walking - Beginning path" |
| CDW | "Downward Inclined Walking - Cyclical path" |
| CGD | "Going Down Stairs - Cyclical path" |
| CGU | "Going Up Stairs - Cyclical path" |
| CTW | "Linear Walking - Cyclical path" |
| CUW | "Upward Inclined Walking - Cyclical path" |
| ECW | "Curve Walking Path" |
| EDW | "Downward Inclined Walking - Ending path" |
| EGD | "Going Down Stairs - Ending path" |
| EGU | "Going Up Stairs - Ending path" |
| ETW | "Linear Walking - Ending path" |
| EUW | "Upward Inclined Walking - Ending path" |
| SDW | "Sitting down" |
| SIT | "Sitting" |
| SAT | "Stance of feet" |
| SUP | "Standing Up" |

Figure 6:
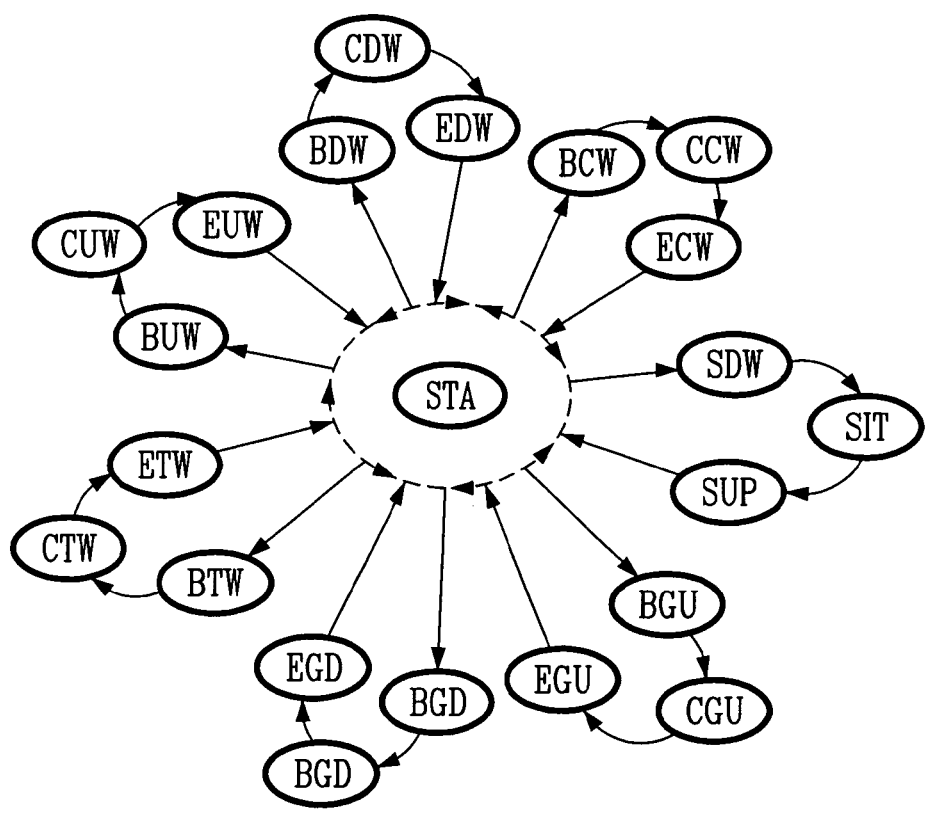
FIG. 6 is an example of a state machine diagram for the selection of the portion of locomotion.

FIG. 6 illustrates an example of the state machine concerning these various portions of locomotion.

FIG. 7 shows an example of a phase sequence mapping, BTW_1 to BTW_25, for the Beginning Path of Linear Walking (BTW) portion of locomotion. All locomotion portions have similar patterns of phase sequence mapping, though the number of phases may vary from one locomotion portion to another. The number of phases depends on the desired granularity of the decomposition of the locomotion portion. The phases are determined experimentally by observing the states of the four localized plantar pressures at specific time intervals, which are determined by the desired granularity. Since a phase is the combination of the states of the four localized plantar pressures, the phase boundary conditions are therefore defined as the combination of each localized plantar pressure state boundary conditions.

For the selection of the portion of locomotion the subject is in, the algorithm uses the state machine approach. For this purpose, the algorithm uses a set of events which values define the conditions, or portion boundary conditions, to pass from one locomotion portion to another. These events are identified by experimentation according to the evolution of the localized plantar pressure signals, the complementary signals and their first three differentials, as well as the signals from the auxiliary artificial proprioceptors, when the subject passes from one locomotion portion to another.

Having determined the states of the main artificial proprioceptors' sensors, the phase of locomotion portion and portion of locomotion of the subject, the TG (44) can be used to calculate one or more dynamic parameter values to be converted to an output signal for the control of the actuator. Examples of dynamic parameter values are the angular displacement and the torque (or moment of force) at the knee joint of the actuated leg prosthesis (12). Since these values are given in real time, they provide what is commonly referred to as the "system's trajectory". At any time k during the subject's locomotion, a mathematical relationship is selected according to the state of the whole system, that is the states of the main artificial proprioceptors, the phase of locomotion portion, the portion of locomotion and the walking speed. Following which, the angular displacement $\theta_{kn}$ and the moment of force $m_{kn}$ are then computed using simple time dependant equations and static characteristics associated with the state of the system, thereby providing the joint's trajectory to the knee joint member. This process is repeated throughout the subject's locomotion.

Figure 8A:
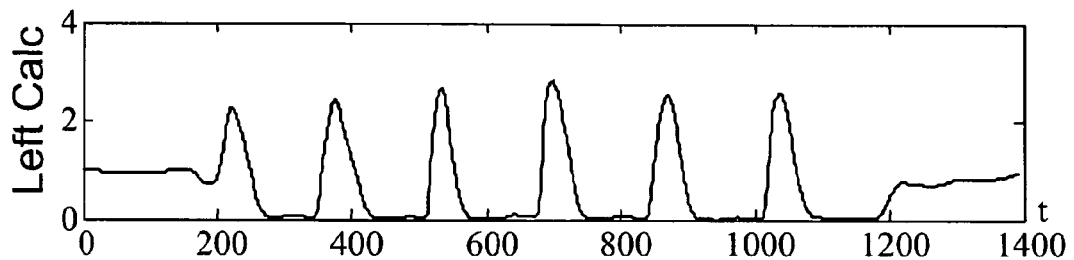
FIGS. 8a to 8d are examples of four data signals using plantar pressure sensors during typical walking on flat ground.
Figure 8B:
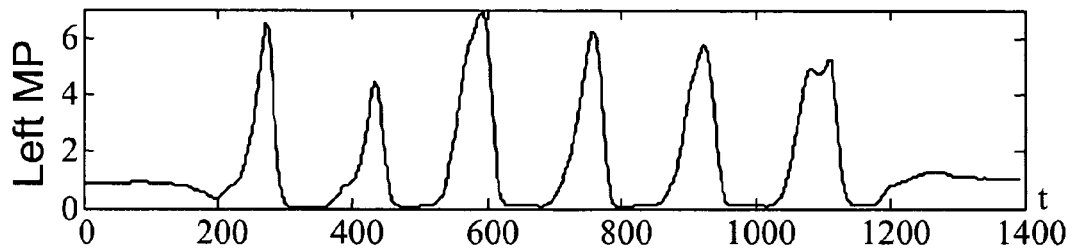
Figure 8C:
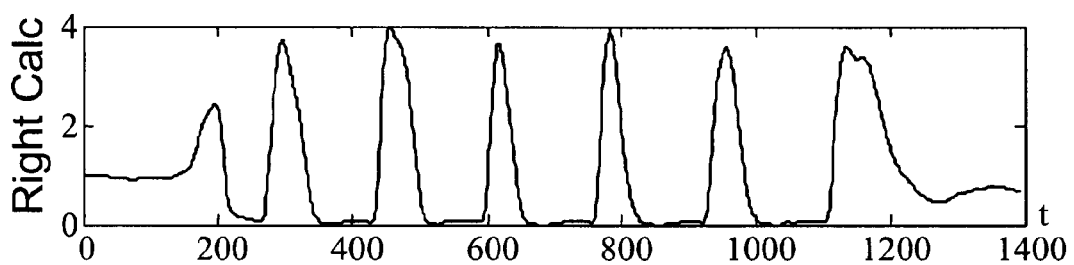
Figure 8D:
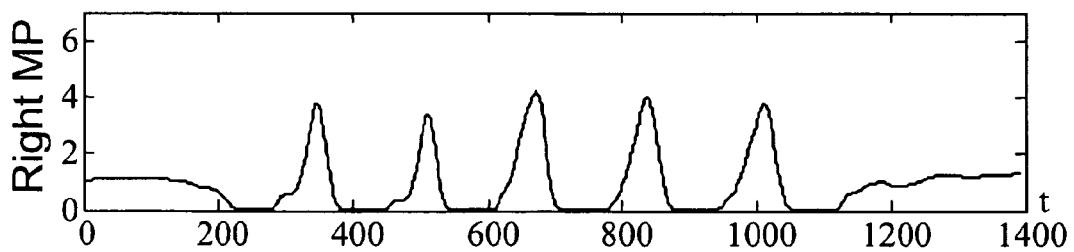
Figure 9A:
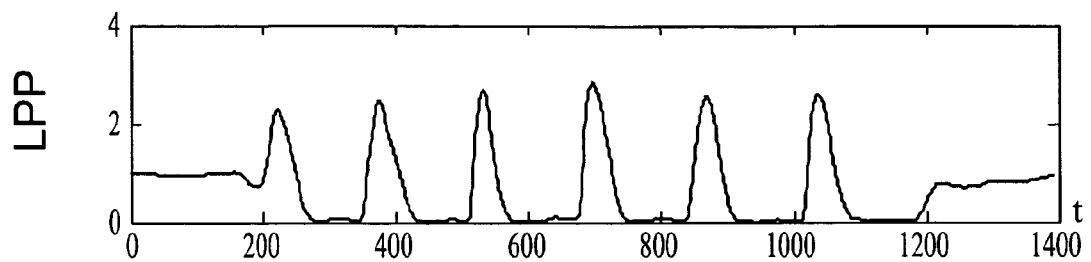
FIGS. 9a to 9d give an example of a data signal obtained from a plantar pressure sensor at the calcaneus region and its first three differentials.
Figure 9B:
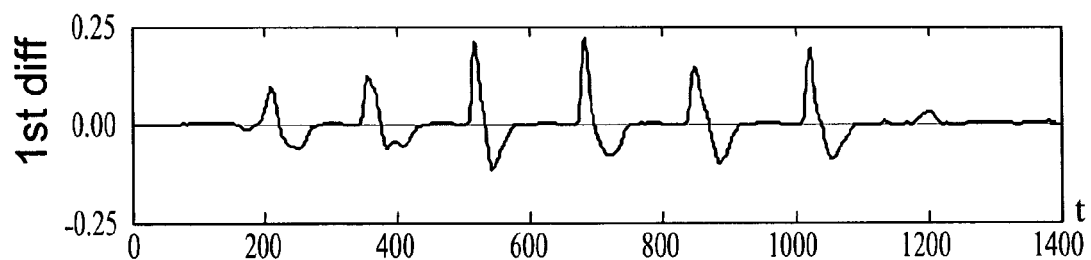
Figure 9C:
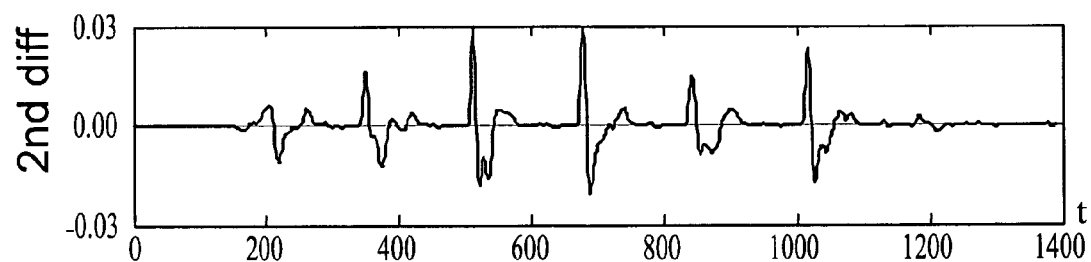
Figure 9D:
Figure 10A:
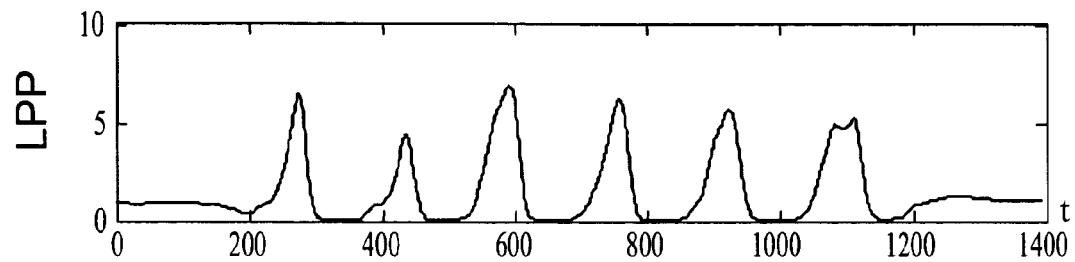
FIGS. 10a to 10d give an example of a data signal obtained from a plantar pressure sensor at the metatarsophalangeal (MP) region and its first three differentials.
Figure 10B:
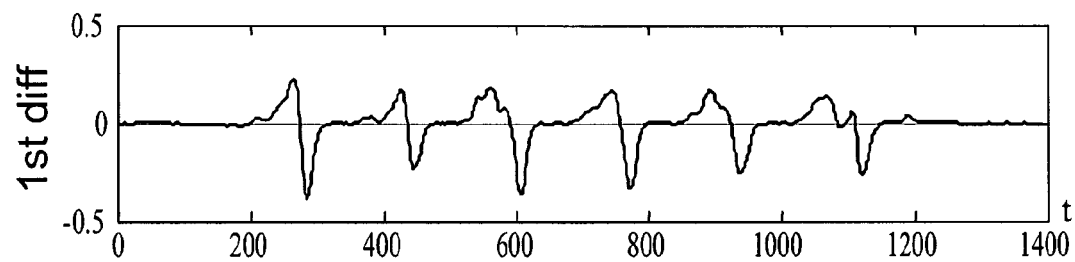
Figure 10C:
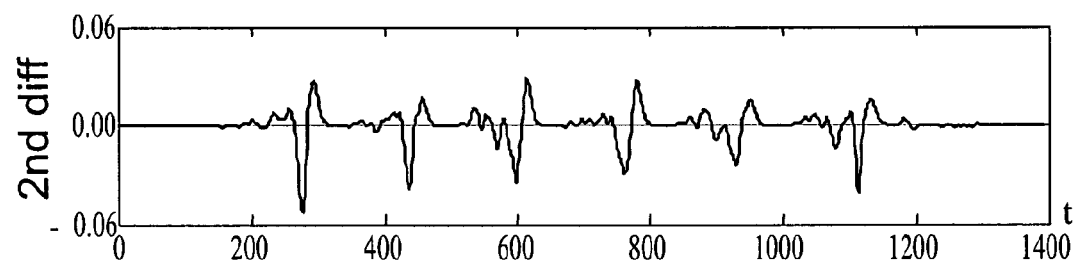
Figure 10D:
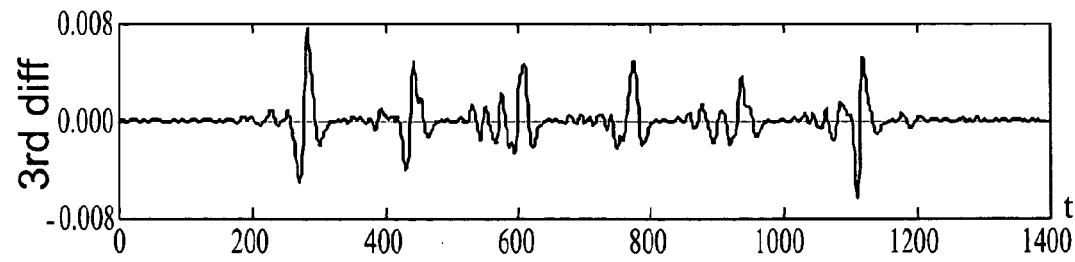
Figure 11A:
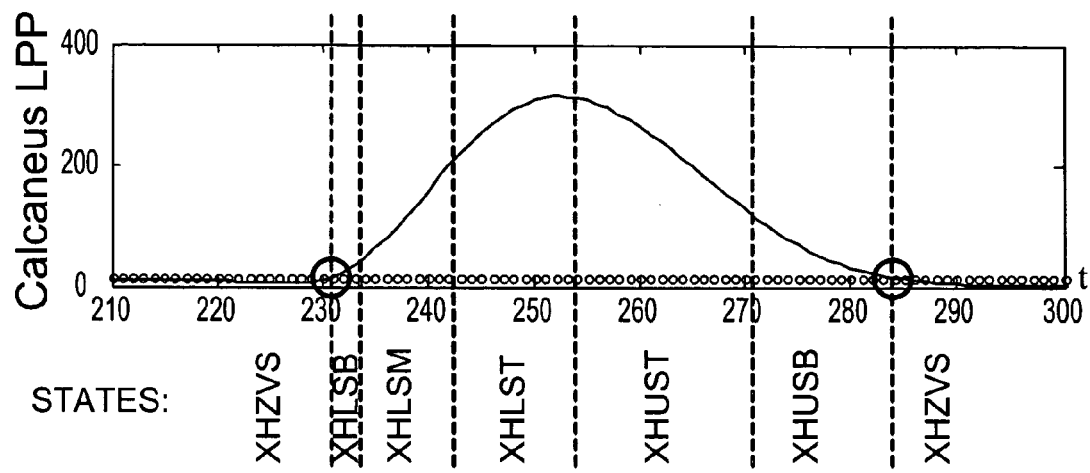
FIGS. 11a to 11d give an example of the states of a plantar pressure sensor with reference to the data signal and its three first differentiations for a plantar pressure sensor at the calcaneous region.
Figure 11B:
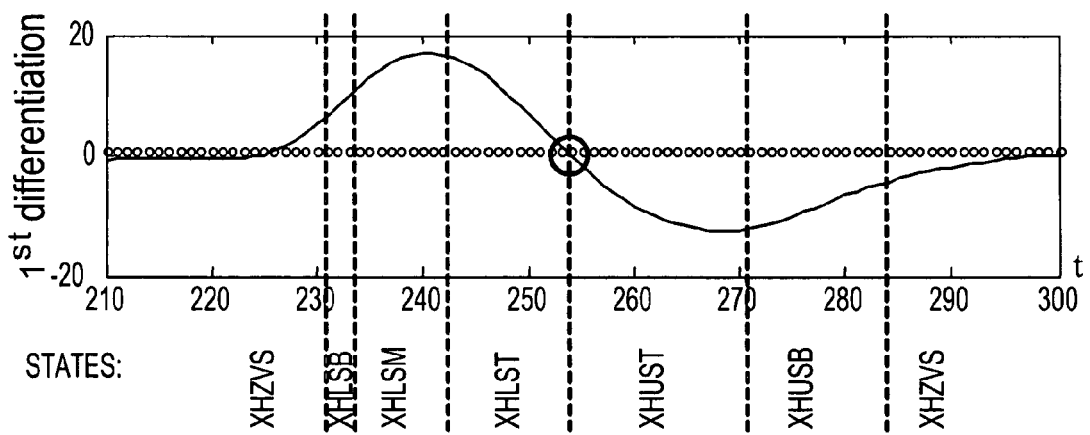
Figure 11C:
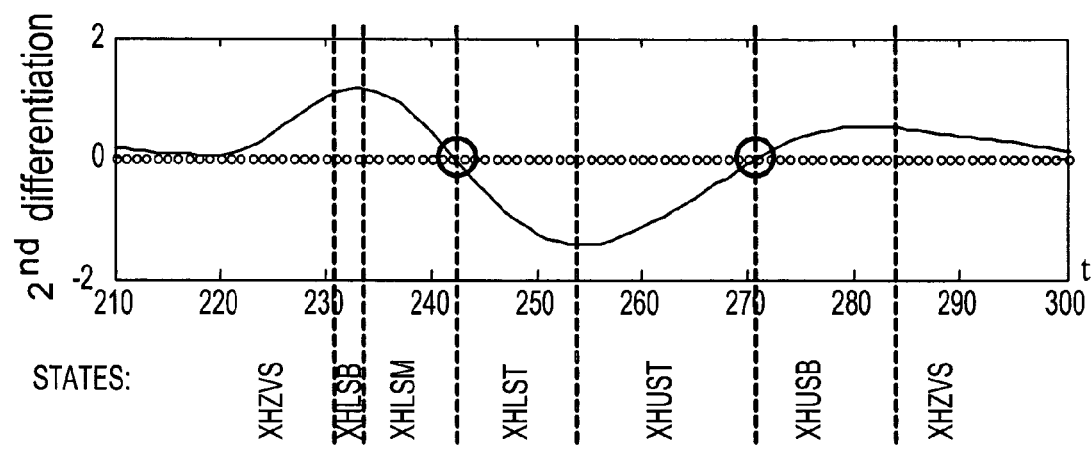
Figure 11D:
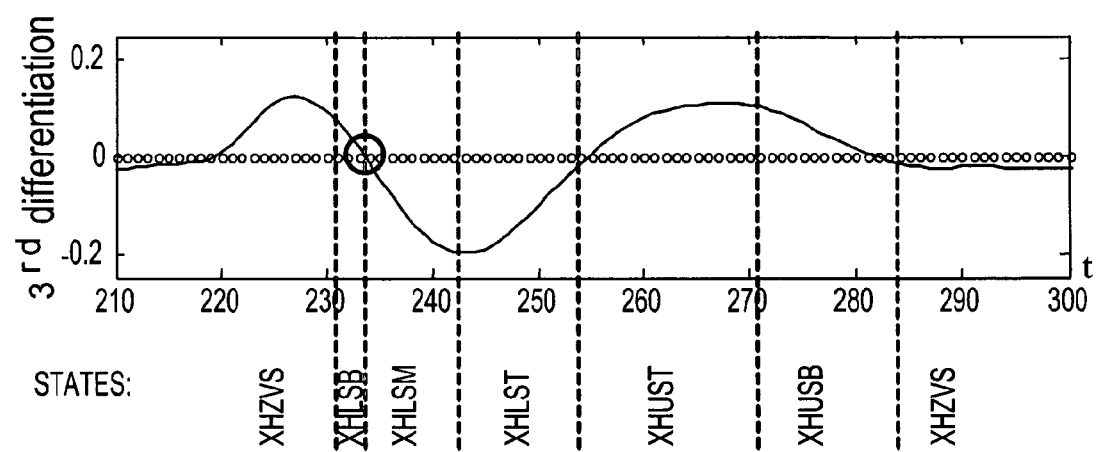

FIGS. 8a to 8d show examples of data signals from the four localized plantar pressure sensors (16) during a standard walking path at 109.5 steps/minute. The four signals, $f_{r1}(t)$, $f_{r2}(t)$, $f_{r3}(t)$ and $f_{r4}(t)$, correspond to the variation in time of the localized plantar pressure at the calcaneus region of the left foot (FIG. 8a), the MP region of the left foot (FIG. 8b), the calcaneus region of the right foot (FIG. 8c), and the MP region of the right foot (FIG. 8d).

In accordance with the present invention, the PRM (42) uses the first, the second and the third differentials of each of those four localized plantar pressure signals in order to determine the sensors' state. From there, the PRM (42) will be able to determine the phase of locomotion portion and portion of locomotion of the subject.

FIGS. 9a to 9d and 10a to 10d show examples of graphs of localized plantar pressures, as well as their first, second and third differentials, at the calcaneus and MP regions respectively, for a linear walking path of 109.5 steps/minute.

Figure 12A:
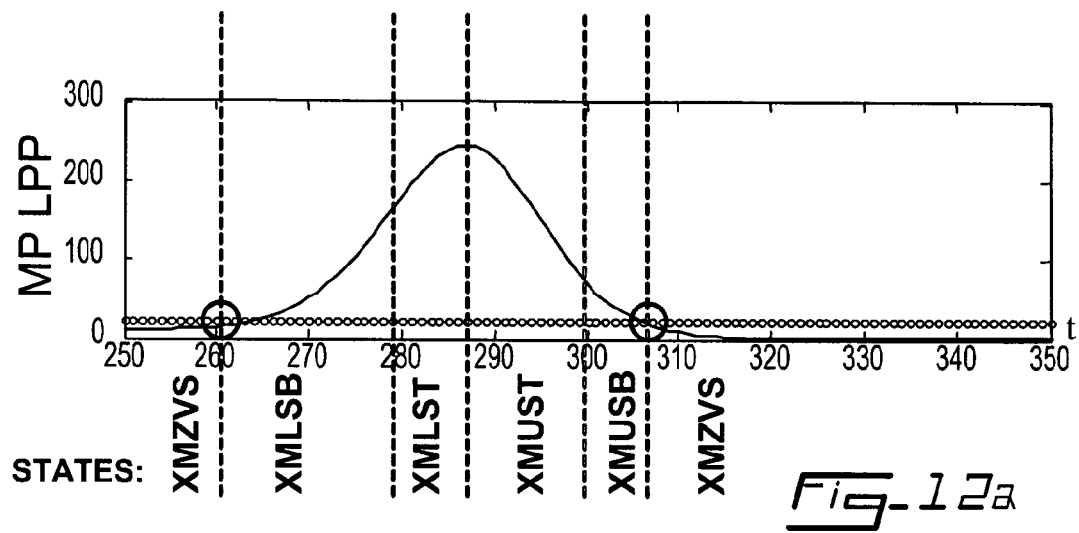
FIGS. 12a to 12c give an example of the states of a plantar pressure sensor with reference to the data signal and its three first differentiation for a plantar pressure sensor at the metatarsophalangeal (MP) region.
Figure 12B:
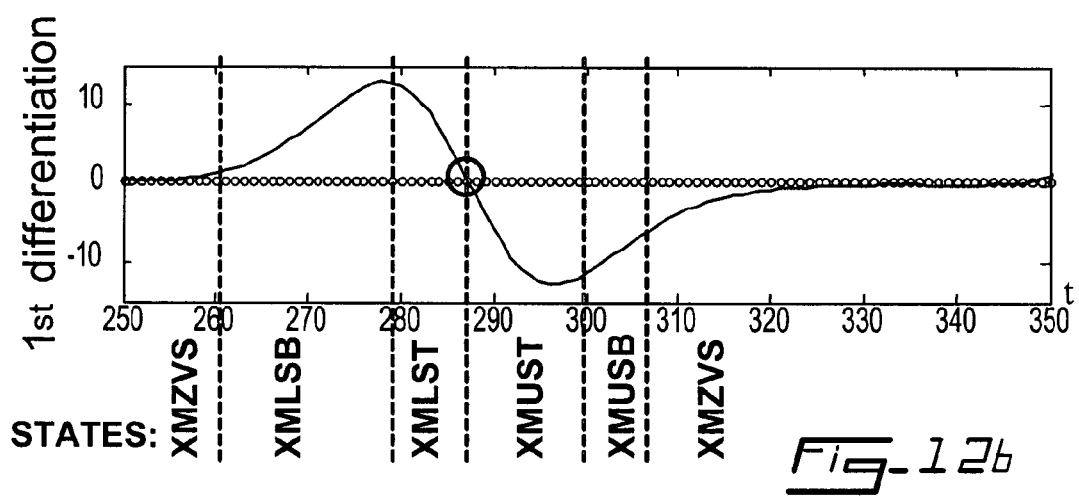
Figure 12C:
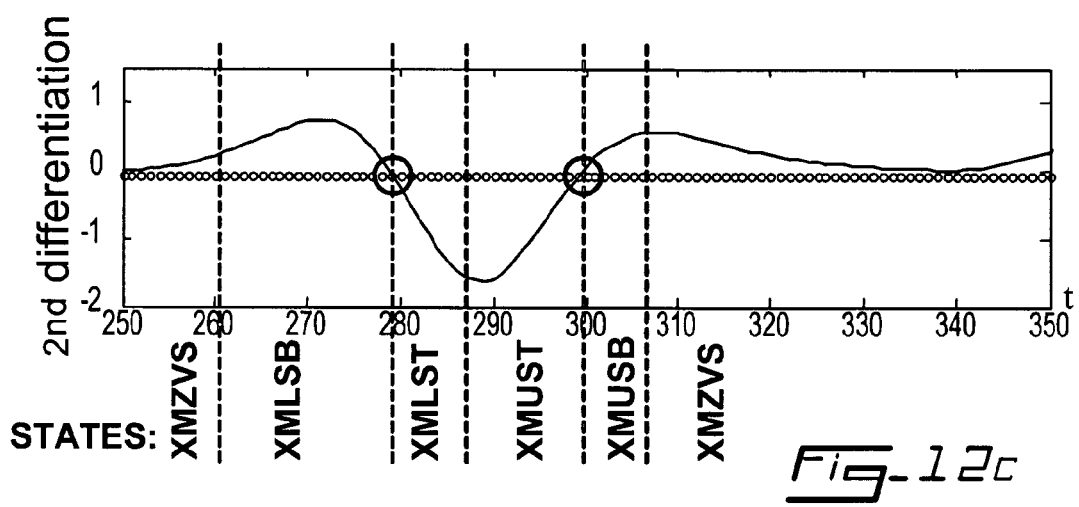

FIGS. 11a to 11d show graphically the state boundary conditions for a typical localized plantar pressure signal, and its first three differentials, at the calcaneous region, while FIGS. 12a to 12c do so for the localized plantar pressure signal, and its first two differentials, at the MP region. This shows the relationships between the various data and derivative signals, and the states.

In use, for the detection of the state of the four localized plantar pressures, denoted $f_{rx}$ where x=[1, 4], the PRM (42) uses a set of first state machines to select, at each increment in time, the current state of each sensor. For this purpose, the algorithm uses a set of events whose values define the conditions to pass from one state to another for each of the localized plantar pressures. Table 2 lists the events:

TABLE 2

List of events used to evaluate the state boundary condition of a localized plantar pressure

| Event | Acronym | Description |
|---|---|---|
| Non-Zero of $f_{rx}$ | FR_BIN$_x$ | Detection of a positive $f_{rx}$ |
| First Differentiation of $f_{rx}$ | FRfst_BIN$_x$ | Detection of positive first differentiation of $f_{rx}$ |
| Second Differentiation of $f_{rx}$ | FRsec_BIN$_x$ | Detection of positive second differentiation of $f_{rx}$ |
| Third Differentiation of $f_{rx}$ | FRtrd_BIN$_x$ | Detection of positive third differentiation of $f_{rx}$ |
| Static $f_{rx}$ | STA_BIN$_x$ | Detection of a static evolution of all $f_{rx}$ |

The conditions placed on the values of each of the depicted events of Table 2 define when the state machines pass from one state to another for each of the localized plantar pressures. Table 3 lists the thresholds used to assess if the aforementioned conditions are met, in which $sum_y$ depicts the five complementary signals, for y=[a, e] as described in Table 4, while Table 5 shows the mathematical form of the events used to evaluate the state boundary condition of the localized plantar pressures.

Figure 13:
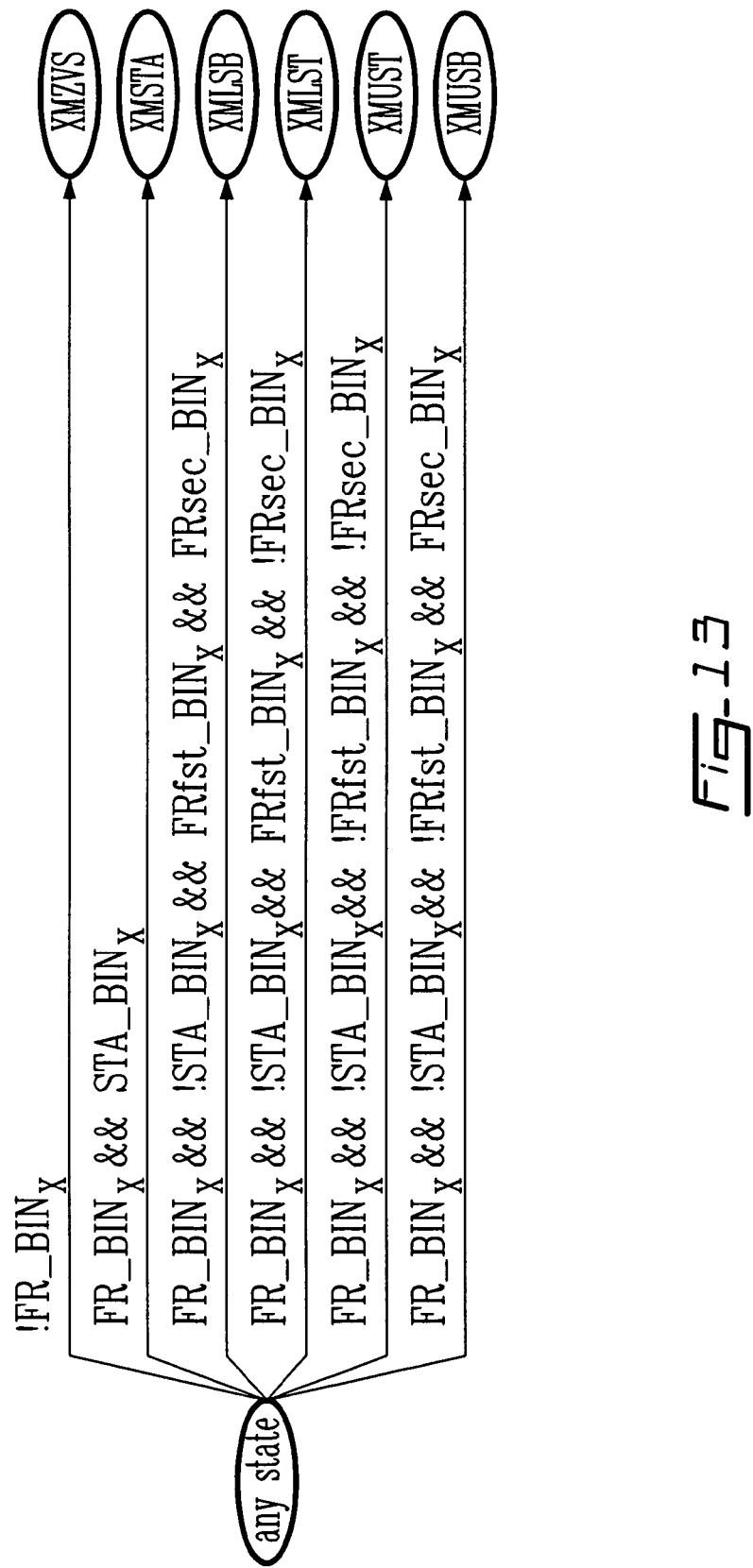
FIG. 13 is an example of a state machine diagram for the selection of the state of the plantar pressure sensors for the calcaneous region.
Figure 14:
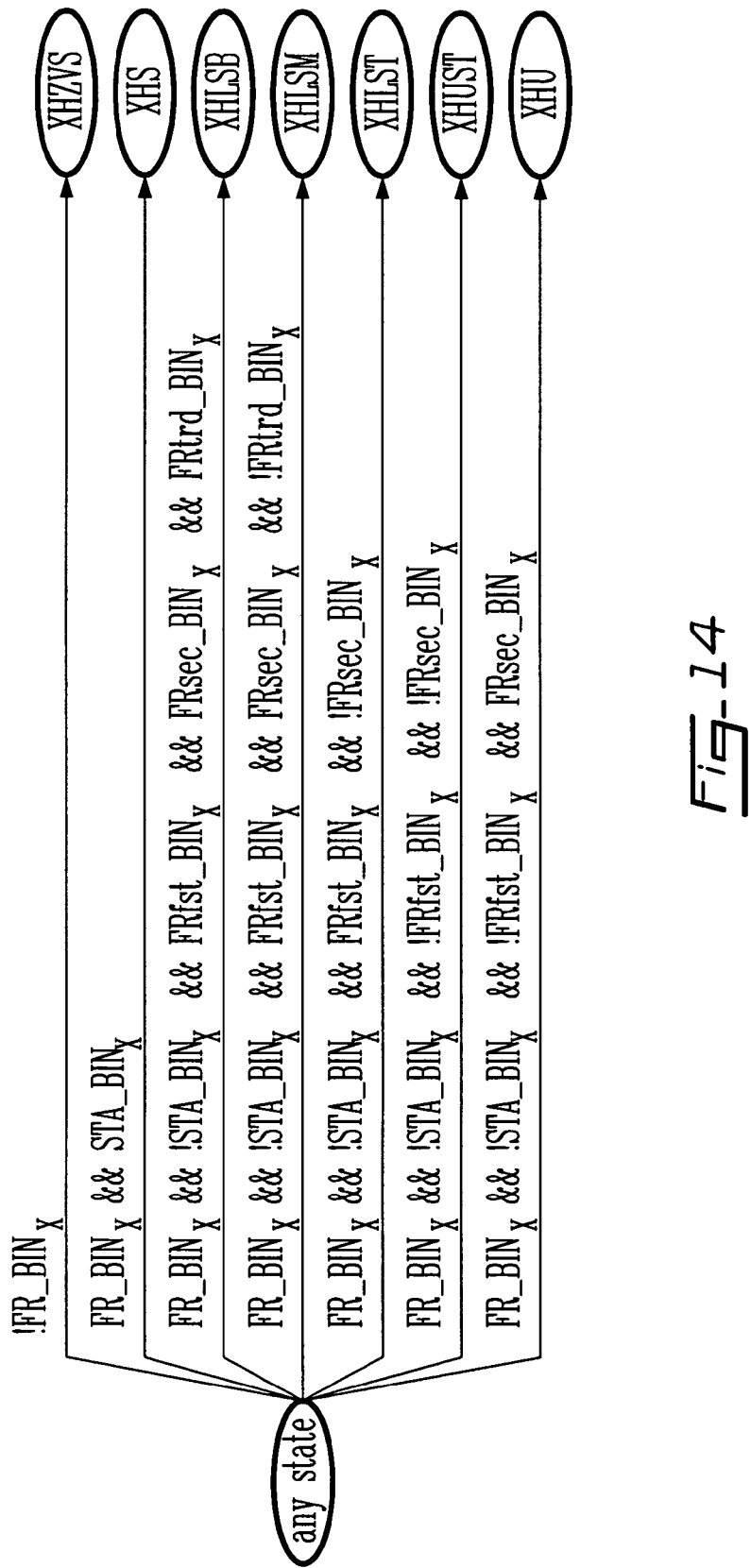
FIG. 14 is an example of a state machine diagram for the selection of the state of the plantar pressure sensors at the metatarsophalangeal (MP) region.

FIGS. 13 and 14 show, respectively, the diagrams of the state machines used for the detection of the state of the localized plantar pressure at the calcaneous and the MP regions, while Tables 6 and 7 summarize the state boundary conditions between the states of each localized plantar pressure.

TABLE 3

List of thresholds used to evaluate the state boundary condition of a localized plantar pressure

| Threshold | Acronym | Description |
|---|---|---|
| Positive value of $f_{rx}$ | $ZV\_FR_x$ | Threshold to consider $f_{rx}$ to be positive |
| Positive value of $\partial f_{rx}/\partial t$ | $ZV\_FRfst_x$ | Threshold to consider the first differentiation of $f_{rx}$ to be positive. |
| Positive value of $\partial^2 f_{rx}/\partial t^2$ | $ZV\_FRsec_x$ | Threshold to consider the second differentiation of $f_{rx}$ to be positive. |
| Positive value of $\partial^3 f_{rx}/\partial t^3$ | $ZV\_FRtrd_x$ | Threshold to consider the third differentiation of $f_{rx}$ to be positive. |
| Position value of $\partial sum_y/\partial t$ | $ZV\_SUMfst$ | Threshold to consider the absolute value of the first differentiation of $sum_y$ to be positive. |
| Positive value of $\partial^2 sum_y/\partial t^2$ | $ZV\_SUMsec$ | Threshold to consider the absolute value of the second differentiation of $sum_y$ to be positive |

TABLE 4

List of complementary signals built from the four localized plantar pressure $f_{r1}$, $f_{r2}$, $f_{r3}$, $f_{r4}$

| Signal | Acronym | Description | Mathematical value |
|---|---|---|---|
| Left foot | $sum_a$ | Localized plantar pressure signal of left foot | $(f_{r1} + f_{r2})/2$ |
| Right foot | $sum_b$ | Localized plantar pressure signal of right foot | $(f_{r3} + f_{r4})/2$ |
| Both calcaneus | $sum_c$ | Localized plantar pressure signal of both calcaneus | $(f_{r1} + f_{r3})/2$ |
| Both MP | $sum_d$ | Localized plantar pressure signal of both MP | $(f_{r2} + f_{r4})/2$ |
| Both feet | $sum_e$ | Localized plantar pressure signal of both feet | $(f_{r1} + f_{r2} + f_{r3} + f_{r4})/4$ |

TABLE 5

Mathematical formulation of events

| Acronym | Mathematical form |
|---|---|
| $FR\_BIN_x$ | $\begin{cases} 0 & \text{if } f_{rx}(k) < ZV\_FR_x \\ 1 & \text{otherwise} \end{cases}$ |
| $FRfst\_BIN_x$ | $\begin{cases} 0 & \text{if } \frac{df_{rx}(k)}{d(k)} < ZV\_FRfst_x \\ 1 & \text{otherwise} \end{cases}$ |
| $FRsec\_BIN_x$ | $\begin{cases} 0 & \text{if } \frac{d^2 f_{rx}(k)}{d^2(k)} < ZV\_FRsec_x \\ 1 & \text{otherwise} \end{cases}$ |
| $FRtrd\_BIN_x$ | $\begin{cases} 0 & \text{if } \frac{d^3 f_{rx}(k)}{d^3(k)} < ZV\_FRtrd_x \\ 1 & \text{otherwise} \end{cases}$ |
| $STA\_BIN$ | $\begin{cases} 0 & \text{if } \left(\left(\left|\frac{dsum_y(k)}{d(k)}\right| > ZV\_SUMfst\right) \| \left(\left|\frac{d^2 sum_y(k)}{d^2(k)}\right| > ZV\_SUMsec\right)\right) \forall y \\ 1 & \text{otherwise} \end{cases}$ |

TABLE 6

List of state boundary conditions defining the states of the main artificial proprioceptors at the calcaneus region

| CURRENT STATE | STATE BOUNDARY CONDITIONS | NEXT STATE |
|---|---|---|
| Any state | $!FR\_BIN_x$ | XHZVS |
| Any state | $FR\_BIN_x$ && $STA\_BIN_x$ | XHSTA |
| Any state | $FR\_BIN_x$ && $!STA\_BIN_x$ && $FRfst\_BIN_x$ && $FRsec\_BIN_x$ && $FRtrd\_BIN_x$ | XHLSB |
| Any state | $FR\_BIN_x$ && $!STA\_BIN_x$ && $FRfst\_BIN_x$ && $FRsec\_BIN_x$ && $!FRtrd\_BIN_x$ | XHLSM |
| Any state | $FR\_BIN_x$ && $!STA\_BIN_x$ && $FRfst\_BIN_x$ && $!FRsec\_BIN_x$ | XHLST |

TABLE 6-continued

List of state boundary conditions defining the states of the
main artificial proprioceptors at the calcaneus region

| CURRENT STATE | STATE BOUNDARY CONDITIONS | NEXT STATE |
|---|---|---|
| Any state | FR_BIN$_x$ && !STA_BIN$_x$ && !FRfst_BIN$_x$ && !FRsec_BIN$_x$ | XHUST |
| Any state | FR_BIN$_x$ && !STA_BIN$_x$ && !FRfst_BIN$_x$ && FRsec_BIN$_x$ | XHUSB |

TABLE 7

List of state boundary conditions defining the states of the main
artificial proprioceptors at metatarsophalangeal region

| CURRENT STATE | STATE BOUNDARY CONDITIONS | NEXT STATE |
|---|---|---|
| Any state | !FR_BIN$_x$ | XMZVS |
| Any state | FR_BIN$_x$ && STA_BIN$_x$ | XMSTA |
| Any state | FR_BIN$_x$ && !STA_BIN$_x$ && FRfst_BIN$_x$ && FRsec_BIN$_x$ | XMLSB |
| Any state | FR_BIN$_x$ && !STA_BIN$_x$ && FRfst_BIN$_x$ && !FRsec_BIN$_x$ | XMLST |
| Any state | FR_BIN$_x$ && !STA_BIN$_x$ && !FRfst_BIN$_x$ && !FRsec_BIN$_x$ | XMUST |
| Any state | FR_BIN$_x$ && !STA_BIN$_x$ && !FRfst_BIN$_x$ && FRsec_BIN$_x$ | XMUSB |

Figure 15:
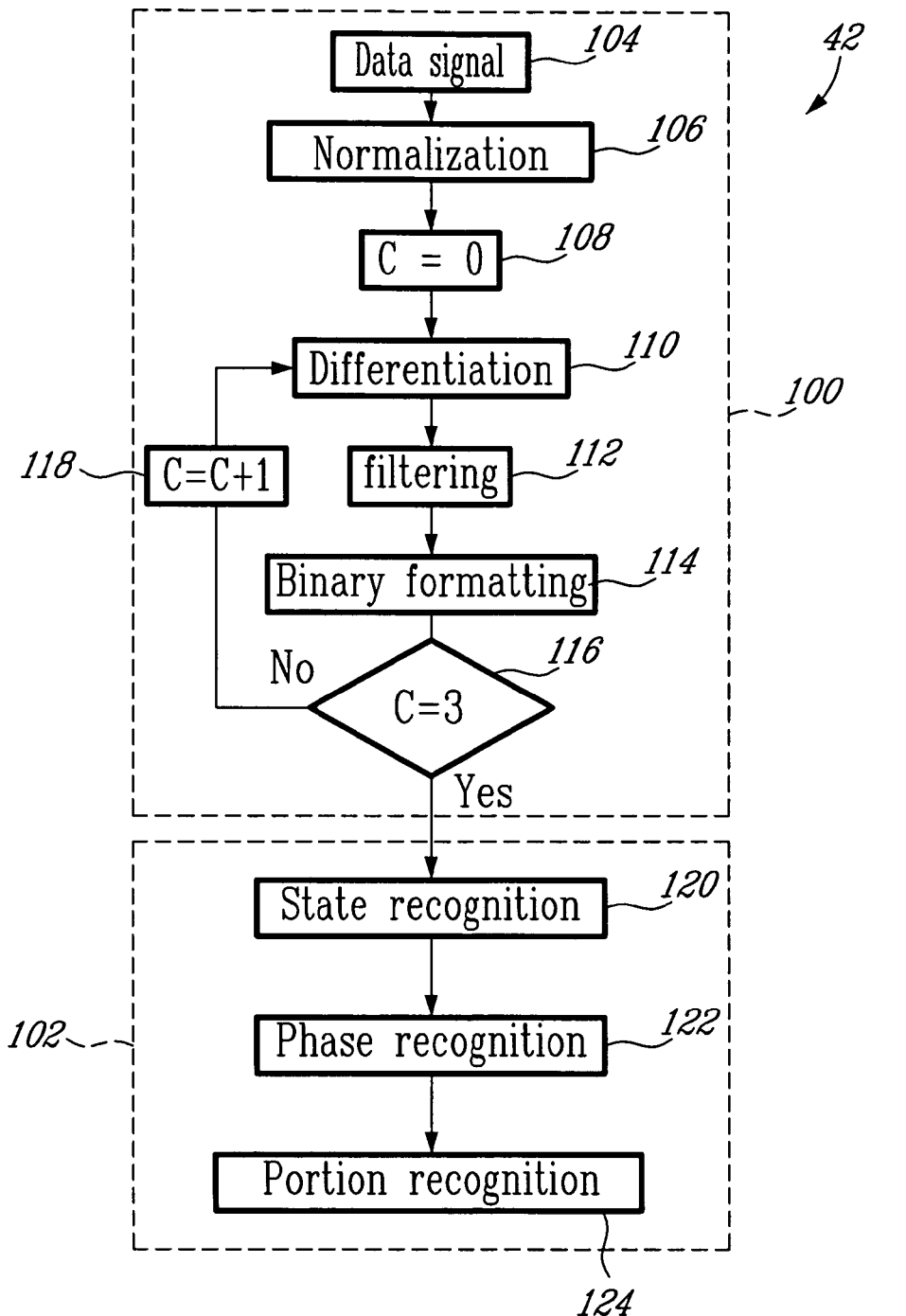
FIG. 15 is an overall block diagram of the Phase Recognition Module (PRM)

FIG. 15 shows a flow chart that depicts the PRM algorithm, which comprises two main parts, namely the pre-processing of the main artificial proprioceptors signals and the locomotion breakdown, illustrated by blocks 100 and 102 respectively. The sequence of steps performed the pre-processing of the main artificial proprioceptors signals, represented by block 100, is indicated by the sequence of blocks 104 to 118. At block 104, the four localized plantar pressures signals are received from the interface and normalized at block 106 using subject specific calibration values. The four normalized local plantar pressures then go through the pre-processing steps represented by blocks 104 to 118. At block 112, the four normalized local plantar pressures are filtered to reduce their spectral composition. A counter is then initialized at block 108, which in turn starts a loop comprising blocks 110 to 116. The first step of the loop, at block 110, consist in the differentiation of the signals. The signals resulting from the differentiation step are filtered at block 112, in order to limit the noise induced during the differential computation, and go through binary formatting at block 114. At block 116, the algorithm checks if the counter has reached 3 iterations. If so, the algorithm, having computed all first three derivatives of the four normalized local plantar pressures signals, exits the loop to block 102. If not, the algorithm proceeds to block 110 where the counter is increased at block 118 and the loop is repeated, in order to computed the next derivative, by proceeding to block 110. When the loop exists to block 102, the algorithm enters into the locomotion breakdown part of the algorithm. The sequence of steps performed by the locomotion breakdown, represented by block 102, is indicated by the sequence of blocks 120 to 124. From the four normalized local plantar pressures and their first three derivatives, block 120 determines the states of each sensor while blocks 122 and 124 determine the phase and the portion of locomotion, respectively.

The normalization step, represented by block 106, consists in levelling the magnitude of the raw data signals according to the anthropomorphic characteristics of the subject such as, in the preferred embodiment, the subject's weight. The raw data signals of the four localized plantar pressures are divided by the total magnitude provided by the four sensors during calibration and then provided as the normalized local plantar pressures to block 110.

At block 112 the normalized raw signals of the four localized plantar pressures and their first three differentials are numerically filtered to reduce their spectral composition, as well as to limit the noise induced during the derivative computation. The preferred embodiment of the PRM (42) uses a 2nd order numerical filter in which the cut-off frequency, the damping factor and the forward shifting have been set, experimentally, to optimize the calculation according to the locomotion portion and the type of signal. The PRM (42) may use other types of numerical filters as well, for example a "Butterworth" filter, as long as the filter's dynamic is similar to the one provided by the 2nd order filter shown thereafter for each locomotion portion. Equation 4 shows the mathematical relationships of the 2nd order numerical filter which is implemented within the PRM (42). Table 8 provides examples of filtering parameters for three different portions of locomotion.

Laplace Form $$H(s) = \frac{\omega_n^2}{s^2 + 2 \cdot \zeta \cdot \omega_n \cdot s + \omega_n^2} \qquad \text{Equation 3}$$

where $\omega_n$ in the nth damping natural frequency, $$\omega_n = \frac{\omega_r}{\sqrt{1 - 2\zeta^2}},$$

$$\zeta < 1$$

$\omega_r$ is called the resonance frequency for $\zeta<1$
$\zeta$ is the damping factor Recursive Form $$H(z) = \frac{b_2 z^{-1} + b_3 z^{-2}}{a_1 + a_2 z^{-1} + a_3 z^{-2}} \qquad \text{Equation 4}$$

$a_1 y(k) =$ $$b_2 x(k-1) + b_3 x(k-2) - a_2 y(k-1) - a_3 y(k-2)$$

where $a_1 = 1$ $a_2 = -2 \cdot \alpha \cdot \beta$ $a_3 = \alpha^2$ $b_1 = 0$ $b_2 = 1 - \alpha \cdot \left[ \beta + \frac{\zeta \cdot \omega_n \cdot \partial}{\omega_r} \right]$ $b_3 = \alpha^2 + \alpha \cdot \left[ \frac{\zeta \cdot \omega_n \cdot \partial}{\omega_r} - \beta \right]$ $\alpha = e^{-\zeta \cdot \omega_n T_e}$ $\beta = \cos(\omega_r T_e)$ $\partial = \sin(\omega_r T_e)$ $T_e$ = sampling rate

TABLE 8

Examples of parameters of 2nd order filters used by the PRM

| Portion of locomotion | Type of signal | Filtering Parameters | | |
|---|---|---|---|---|
| | | Cut-Off Frequency ($F_c$) | Damping Factor (z) | Forward Shifting |
| Linear Walking - Beginning path (BTW) | Raw | 2 | 0.680 | 7 |
| | Derivative | 3 | 0.700 | 3 |
| Linear Walking - Cyclical path (CTW) | Raw | 2 | 0.680 | 7 |
| | Derivative | 3 | 0.700 | 3 |
| Linear Walking - Ending path (ETW) | Raw | 2 | 0.680 | 7 |
| | Derivative | 3 | 0.700 | 3 |

At block 110, the derivatives are obtained by the standard method consisting of numerically differentiating the current and the previous samples of localized plantar pressures.

The derivatives obtained at block 110 then go through binary formatting at block 114. The result of the binary formatting operation will be a "1" if the sign of the derivative is positive, "0" if it is negative. This step facilitates the identification of the sign changes of the differentiated signals as binary events.

At block 120, the PRM (42) determines the current state of each sensor using state machines such as the ones shown in FIGS. 13 and 14.

In the PRM (42), the states of the localized plantar pressures are preferably expressed as a 10-bit words in which each bit corresponds to a specific possible state. Tables 9 to 12 list the binary equivalents of each state of the localized plantar pressures at the calcaneous and the MP regions of the left and the right foot. Of course, words of different bit length may be used as well to represent the state of each localized plantar pressure.

TABLE 9

Numerical labels of the states for the localized plantar pressure at calcaneous area of the left foot

| STATE | BINARY LABEL | DECIMAL LABEL |
|---|---|---|
| LHSBS | 0 0 0 0 0 0 0 0 0 1 | 0 |
| LHLSB | 0 0 0 0 0 0 0 0 1 0 | 1 |
| LHLSM | 0 0 0 0 0 0 0 1 0 0 | 2 |
| LHLST | 0 0 0 0 0 0 1 0 0 0 | 3 |
| LHUST | 0 0 0 0 0 1 0 0 0 0 | 4 |
| LHUSM | 0 0 0 0 1 0 0 0 0 0 | 5 |
| LHUSB | 0 0 0 1 0 0 0 0 0 0 | 6 |
| LHZVS | 0 0 1 0 0 0 0 0 0 0 | 7 |
| LHSTA | 0 1 0 0 0 0 0 0 0 0 | 8 |

TABLE 10

Numerical labels of the states for the localized plantar pressure at metatarsophalangeal area of the left foot

| STATE | BINARY LABEL | DECIMAL LABEL |
|---|---|---|
| LMSBS | 0 0 0 0 0 0 0 0 0 1 | 0 |
| LMLSB | 0 0 0 0 0 0 0 0 1 0 | 1 |
| LMLSM | 0 0 0 0 0 0 0 1 0 0 | 2 |
| LMLST | 0 0 0 0 0 0 1 0 0 0 | 3 |
| LMUST | 0 0 0 0 0 1 0 0 0 0 | 4 |
| LMUSM | 0 0 0 0 1 0 0 0 0 0 | 5 |

TABLE 10-continued

Numerical labels of the states for the localized plantar pressure at metatarsophalangeal area of the left foot

| STATE | BINARY LABEL | DECIMAL LABEL |
|---|---|---|
| LMUSB | 0 0 0 1 0 0 0 0 0 0 | 6 |
| LMZVS | 0 0 1 0 0 0 0 0 0 0 | 7 |
| LHSTA | 0 1 0 0 0 0 0 0 0 0 | 8 |

TABLE 11

Numerical labels of the states for the localized plantar pressure at calcaneous area of the right foot

| STATE | BINARY LABEL | DECIMAL LABEL |
|---|---|---|
| RHSBS | 0 0 0 0 0 0 0 0 0 1 | 0 |
| RHLSB | 0 0 0 0 0 0 0 0 1 0 | 1 |
| RHLSM | 0 0 0 0 0 0 0 1 0 0 | 2 |
| RHLST | 0 0 0 0 0 0 1 0 0 0 | 3 |
| RHUST | 0 0 0 0 0 1 0 0 0 0 | 4 |
| RHUSM | 0 0 0 0 1 0 0 0 0 0 | 5 |
| RHUSB | 0 0 0 1 0 0 0 0 0 0 | 6 |
| RHZVS | 0 0 1 0 0 0 0 0 0 0 | 7 |
| RHSTA | 0 1 0 0 0 0 0 0 0 0 | 8 |

TABLE 12

Numerical labels of the states for the localized plantar pressure at metatarsophalangeal area of the right foot

| STATE | BINARY LABEL | DECIMAL LABEL |
|---|---|---|
| RMSBS | 0 0 0 0 0 0 0 0 0 1 | 0 |
| RMLSB | 0 0 0 0 0 0 0 0 1 0 | 1 |
| RMLSM | 0 0 0 0 0 0 0 1 0 0 | 2 |
| RMLST | 0 0 0 0 0 0 1 0 0 0 | 3 |
| RMUST | 0 0 0 0 0 1 0 0 0 0 | 4 |
| RMUSM | 0 0 0 0 1 0 0 0 0 0 | 5 |
| RMUSB | 0 0 0 1 0 0 0 0 0 0 | 6 |
| RMZVS | 0 0 1 0 0 0 0 0 0 0 | 7 |
| RHSTA | 0 1 0 0 0 0 0 0 0 0 | 8 |

At block 122, the PRM (42) generates the phase, which is preferably expressed as the direct binary combination of the states of the four localized plantar pressures. Accordingly, the phase can be represented by a 40-bit word wherein the lower part of the lower half word, the higher part of the lower half word, the lower part of the higher half word and the higher part of the higher half word correspond, respectively, to the calcaneous area of the left foot, the MP area of the left foot, the calcaneous area of the right foot and the MP area of the right foot, as represented in Tables 9 to 12. Table 13 presents an example of the identification of a phase from the states of the four localized plantar pressures.

TABLE 13

Identification of a phase from the states of the main artificial proprioceptors

State of Localized Plantar Pressure

| Right Foot | | Left Foot | | |
|---|---|---|---|---|
| MP area | Calcaneous | MP area | Calcaneous | Corresponding Phase |
| 0000000100 | 0000010000 | 0000000001 | 0000010000 | 00000001000000010000 |
| | | | | 00000000010000010000 |

At block 124, the PRM (42) selects the portion of locomotion the subject is currently using the state machine shown in FIG. 6. Each portion of locomotion is composed of a sequence of phases.

Accordingly, Table 14 presents the phases sequence mapping for the Beginning Path of Linear Walking (BTW) locomotion portion corresponding to FIG. 7. This table shows the label, the decimal value and as well the phase boundary conditions of each phase.

TABLE 14

Example of phases sequence mapping for the locomotion portion labeled "Beginning Path of Linear Walking" (BTW)

| | Phase | Phase Boundary Conditions | | | |
|---|---|---|---|---|---|
| Label | Value | $F_{r1}$ | $F_{r2}$ | $F_{r3}$ | $F_{r4}$ |
| BTW_1 | 27516604800 | 8 | 8 | 8 | 8 |
| BTW_2 | 3449396416 | 5 | 7 | 3 | 7 |
| BTW_3 | 2281717888 | 1 | 7 | 4 | 7 |
| BTW_4 | 4429217920 | 2 | 7 | 5 | 7 |
| BTW_5 | 17213489280 | 4 | 5 | 6 | 7 |
| BTW_6 | 1731119808 | 4 | 7 | 5 | 7 |
| BTW_7 | 34493988992 | 5 | 7 | 5 | 7 |
| BTW_8 | 34494087296 | 5 | 7 | 7 | 7 |
| BTW_9 | 3436186816 | 5 | 1 | 5 | 7 |
| BTW_10 | 34361966720 | 5 | 1 | 7 | 7 |
| BTW_11 | 68723802240 | 6 | 2 | 7 | 7 |
| BTW_12 | 68727996544 | 6 | 3 | 7 | 7 |
| BTW_13 | 68727867520 | 6 | 3 | 1 | 7 |
| BTW_14 | 137455732864 | 7 | 4 | 1 | 7 |
| BTW_15 | 137455734912 | 7 | 4 | 2 | 7 |
| BTW_16 | 137455739008 | 7 | 4 | 3 | 7 |
| BTW_17 | 13772512128 | 7 | 5 | 2 | 7 |
| BTW_18 | 13772516224 | 7 | 5 | 3 | 7 |
| BTW_19 | 1377252416 | 7 | 5 | 4 | 7 |
| BTW_20 | 137573187712 | 7 | 7 | 4 | 7 |
| BTW_21 | 137573204096 | 7 | 7 | 5 | 7 |
| BTW_22 | 137573187586 | 7 | 7 | 4 | 1 |
| BTW_23 | 137573203970 | 7 | 7 | 5 | 1 |
| BTW_24 | 137573236740 | 7 | 7 | 6 | 2 |
| BTW_25 | 137573236744 | 7 | 7 | 6 | 3 |

Table 15 enumerates a sample of boundary conditions associated with the locomotion portion of the sitting and typical walking on flat ground movements, while Table 3 lists the thresholds used to assess if the aforementioned conditions are met.

TABLE 15

Example of a list of portion boundary conditions defining specific locomotion portions such as sitting movements (STA-SUP-SIT-SDW-STA locomotion portion) and typical walking on flat ground (STA-BTW-CTW-ETW-STA locomotion portion)

| Current Portion | Set of Events | Next Portion |
|---|---|---|
| STA | $SWING_{leg}$ | BTW |
| | $!STATIC\_GR_{leg}$ \|\| $!STATIC\_GR_{prost}$ | |
| | $FR\_LOW_{prost\_heel}$ | |
| | $FR\_BIN_{leg\_heel}$ | |
| | BTW_SWING | |
| | $FR\_HIGH_{leg\_heel}$ | SDW |
| | $FR\_HIGH_{prost\_heel}$ | |
| | PKA_SDW | |
| BTW | $STATIC\_GR_{leg}$ | ETW |
| | $STATIC\_GR_{prost}$ | |
| | $SUM\_BIN_{prost}$ | CTW |
| | $SWING_{prost}$ | |
| CTW | $STATIC\_GR_{leg}$ | STA |
| | $STATIC\_GR_{prost}$ | |
| | $FR\_BIN_{prost\_heel}$ | ETW |
| | $FR\_BIN_{leg\_heel}$ | |
| | PKA_ETW | |
| | $STATIC\_GR_{leg}$ \|\| $STATIC\_GR_{prost}$ | |
| ETW | PKA_STA | STA |
| SDW | PKA_SIT | SIT |
| | PKA_STA | STA |
| SIT | $GR\_POS_{leg}$ | SUP |
| | MIN_SIT | |
| | $FR\_HIGH_{leg\_mp}$ | |
| | $FR\_HIGH_{prost\_mp}$ | |
| | PKA_STA | STA |
| SUP | $!SUM\_BIN_{prost}$ | SIT |
| | $!SUM\_BIN_{leg}$ | |
| | PKA_STA | STA |
| | !PKA_SUP_RAMP | SIT |

TABLE 16

Example of a list of events used to evaluate the portion boundary conditions defining specific locomotion portions such as sitting movements (STA-SUP-SIT-SDW-STA locomotion portion) and typical waking on flat ground (STA-BTW-CTW-ETW-STA locomotion portion)

| Event | Acromyn | Description |
|---|---|---|
| Swing occurence | $SWING_y$ | Detection of a swing prior to a foot strike |
| Non-Zero of $f_{rx}$ | $FR\_BIN_x$ | Detection of a positive $f_{rx}$ |
| Low $f_{rx}$ | $FR\_LOW_x$ | Detection of $f_{rx}$ level between the zero envelope and the STA envelope |
| High $f_{rx}$ | $FR\_HIGH_x$ | Detection of $f_{rx}$ level above the STA envelope |
| Static $g_{ry}$ | $STATIC\_GR_y$ | Detection of $g_{ry}$ level below the zero angular speed envelope and the zero acceleration envelope |
| Non-Zero of $sum_y$ | $SUM\_BIN_y$ | Detection of a positive $sum_y$ |
| BTW swing occurrence | BTW_SWING | Detection of typical walking $g_{r\_leg}$ during leg swing |
| Positive $g_{ry}$ | $GR\_POS_y$ | Detection of a positive $g_{ry}$ |
| Minimum sitting | MIN_SIT | Detection of a minimum time in portion SIT |
| Sit down knee angle | PKA_SDW | Detection of knee angle higher than the STA envelope |
| End walking knee angle | PKA_ETW | Detection of knee angle lower than the STA envelope |
| Stance knee angle | PKA_STA | Detection of knee angle lower than the STA envelope |
| Sit down knee angle | PKA_SIT | Detection of knee angle higher than the SIT envelope |
| Standing up knee angle | PKA_SUP_RAMP | Detection of standing up knee angle evolution | where
X stands for leg_heel, leg_mp, prosthetic_heel or prosthetic_mp
Y stands for leg or prosthesis The normalization step of block 106 uses specific calibration values. These values are computed the first time a subject uses the actuated prosthesis (12) or at any other time as may be required. Two calibration values are preferably used: the zero calibration value and the subject's weight calibration value. The zero calibration value consists in the measurement of the four localized plantar pressures when no pressure is applied to the sensors, while the subject's weight calibration value is the subject's weight relative to the magnitude of the total response of the sensors.

Figure 16:
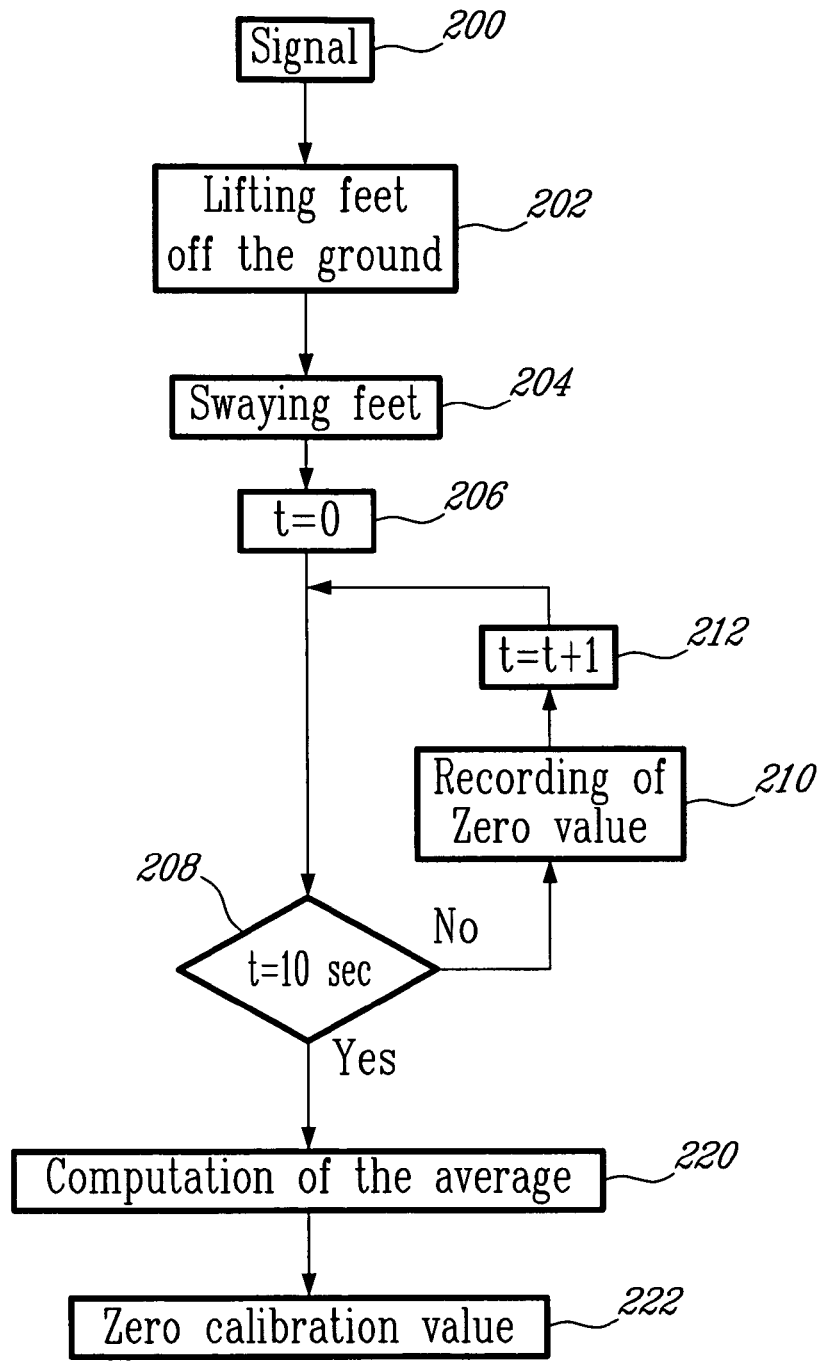
FIG. 16 is a block diagram showing the zero calibration.

The algorithm to obtain the zero calibration value of the sensors is depicted by the flow chart shown in FIG. 16. The sequence of steps composing the algorithm is indicated by the sequence of blocks 200 to 222. In block 200, the algorithm starts with the four localized plantar pressures. At block 202, the subject sits on a surface high enough such that his feet hang freely in the air. Then, at block 204, the subject lightly swings his feet back and forth, which initialises a timer at block 206, which in turn starts a loop comprising blocks 208, 210 and 212. At block 208, the algorithm checks if the timer has reached 10 seconds, if so, then the algorithm exits the loop to block 220, if not, the algorithm proceeds to block 210 and records the zero value of the four sensors. Then, at block 212, the timer is increased and the loop is repeated by proceeding to block 208. At block 220, the average of each localized plantar pressures is computed and finally provided as the zero calibration value at block 222.

Figure 17:
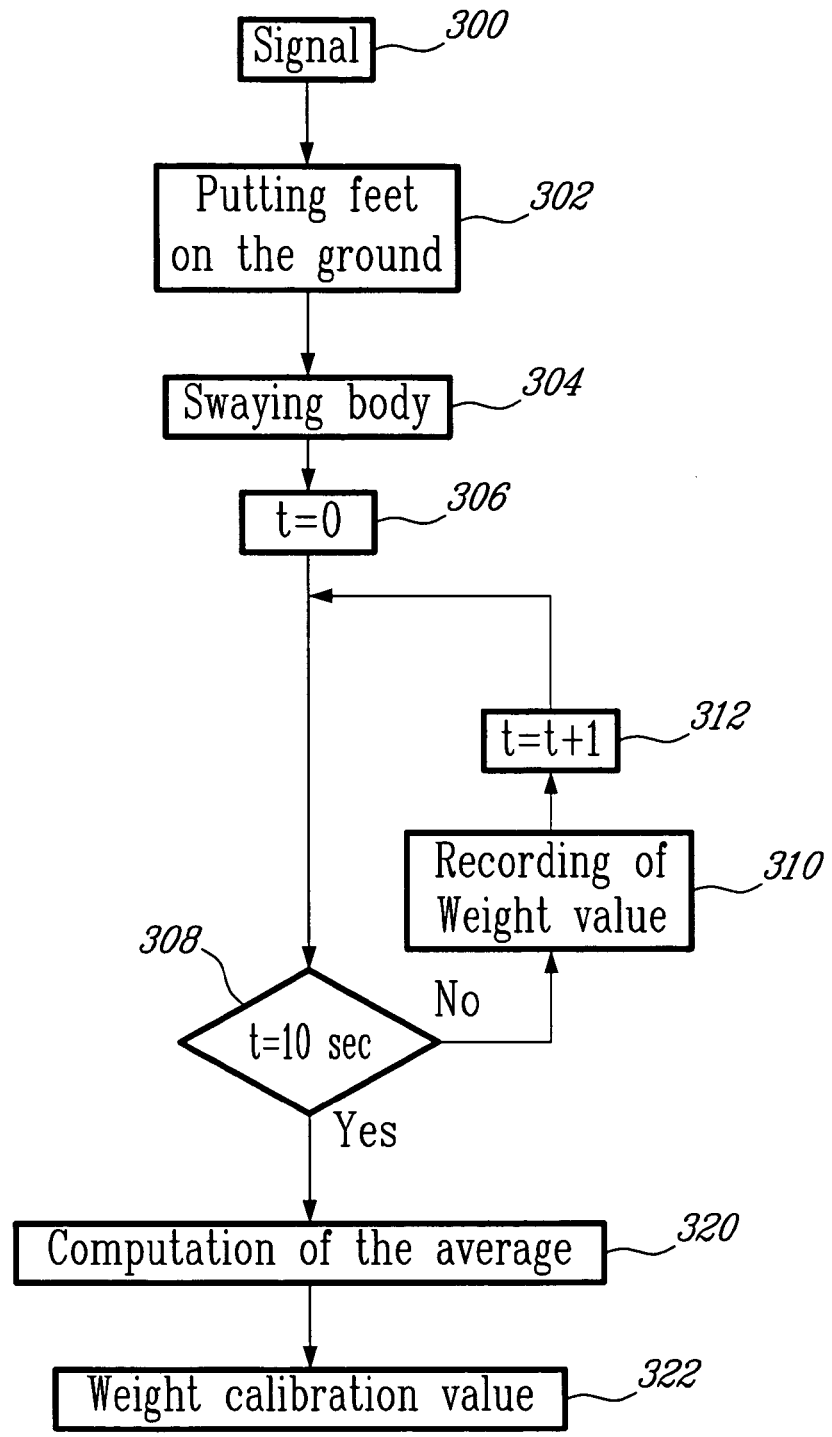
FIG. 17 is a block diagram showing the subject's weight calibration.

In a similar fashion, the algorithm to obtain the subject's weight calibration value is depicted by the flow chart shown in FIG. 17. The sequence of steps composing the algorithm is indicated by the sequence of blocks 300 to 322. In block 300, the algorithm starts with the four localized plantar pressure. At block 302, the subject stands up in a comfortable position, feet at shoulder width distance, while maintaining the body in the stance position. Then, at block 304, the subject slowly swings back and forth and then left to right, which initialises a timer at block 306, which in turn starts a loop comprising blocks 308, 310 and 312. At block 308, the algorithm checks if the timer has reached 10 seconds, if so, then the algorithm exists the loop to block 320, if not, the algorithm proceeds to block 310 and records the subject's weight relative to the magnitude of the total response of the sensors. Then, at block 312, the timer is increased and the loop is repeated by proceeding to block 308. At block 320, the average of each localized plantar pressures is computed and finally provided as the weight calibration value at block 322.

Figure 18:
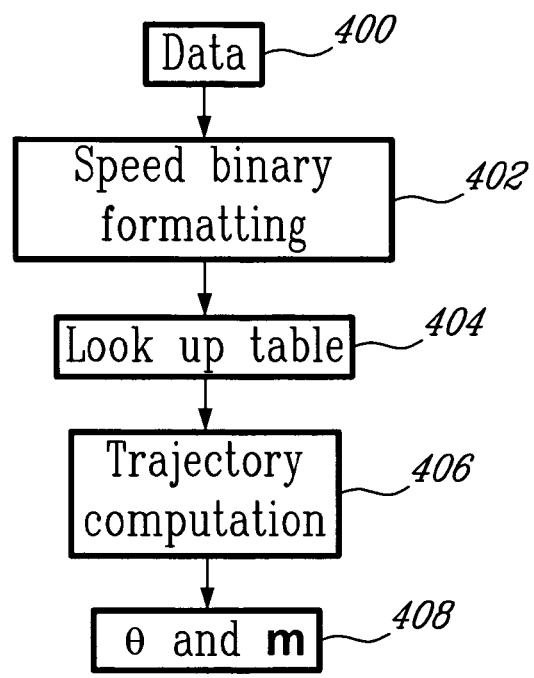
FIG. 18 is a block diagram of the Trajectory Generator (TG)

FIG. 18 shows a flow chart that depicts the TG algorithm used to establish a relationship, in real-time, between the output of the PRM (42) and localized plantar pressures and the knee joint trajectory. The sequence of steps composing the algorithm is indicated by the sequence of blocks 400 to 408. At block 400, the algorithm receives the normalized localized plantar pressures, the phase of locomotion portion and the portion of the locomotion from the PRM (42). Then, at block 402, the walking speed of the subject, in steps per minute, is obtained from computing the number of frames between two heel strikes, while taking into account the sampling frequency, and is binary formatted. More specifically, the subject's speed estimate [k] (steps/minute) is obtained from computing the number of frames between two heel strikes $s_{heel}[k]$ (frames/step):

$$\hat{x}_v = 60 \frac{f_s}{s_{heel}[k] - s_{heel}[k-1]} \qquad \text{Equation 5}$$

where $f_s$ is the frame sampling frequency (frames/second).

A heel strike event occurs when:

$$\text{THRESHOLDHEELLOADING} < f_{rij}[k] - f_{rij}[k-1]_p$$
$$i_j = 1,3 \qquad \text{Equation 6}$$

At block 404, the algorithm uses the normalized localized plantar pressures, the phase of locomotion portion, the portion of the locomotion and the subject's speed in binary format to identify a set of linear normalized static characteristics linking the knee joint kinetic/kinematic parameters with the subject's locomotion in a lookup table. At block 406 the TG (44) comprises two transformation functions which compute the kinetic/kinematic parameters at time k, which are the angular displacement $\theta_{kn}(k)$ and the moment of force (torque) $m_{kn}(k)$, using the localized plantar pressures and their corresponding mathematical relationships (time-dependant equations and static characteristics) identified at block 404. The values of the kinetic/kinematic variables are then provided to the REG (48) at block 408.

The transformation functions used by the TG (44) at block 406 may generally be represented by a system of equations such as:

$$\theta_{g,h}(k) = \Omega_1(\theta_1(k), \chi(k), v(k)) + \Omega_2(\theta_2(k)\chi(k), v(k)) + \ldots + \Omega_{q-1}(\theta_{q-1}(k), \chi(k), v(k)) + \Omega_q(\theta_q(k), \chi(k), v(k))$$

Equation 7

$$m_{g,h}(k) = M_1(\theta_1(k), \chi(k), v(k)) + M_2(\theta_2(k), \chi(k), v(k)) + \ldots + M_{q-1}(\theta_{q-1}(k), \chi(k), v(k)) + M_q(\theta_q(k), \chi(k), v(k))$$

Equation 8 where
g=[sagittal (sg), frontal (fr), transversal (tr)] is the plane of the motion
h=[hip (hp), knee (kn), ankle (an), metatarsophalangeal (mp)] is the joint
q is the number of the main artificial proprioceptors' sensors
$\theta_q$ is the phenomenological entity related to the locomotion and provided by the main artificial proprioceptors' sensors
$\Omega_q$ is the transformation function between the phenomenological entity related to the locomotion, the kinematic variables of the lower extremities and the time
$M_q$ is the transformation function between the phenomenological entity related to the locomotion, the kinetic variables of the lower extremities and the time
$\chi(k) = \Omega(p_h(k), p_r(k), v(k))$ is the state of the whole system (amputee and the AAP) in which k is the current increment
$p_h(k)$ is the phase of the respective locomotion portion
$p_r(k)$ is the locomotion portion
$v(k)$ is the walking speed
k is the current increment In the case where the TG (44) uses polynomial relationships of order n, Equation 7 and Equation 8 become:

$$\theta_{g,h}(k) = a_{1,1}(\chi(k),v(k)) \cdot \theta_1(k) + \ldots + a_{1,n}(\chi(k),v(k)) \cdot \theta_1(k)^n + a_{2,1}(\chi(k),v(k)) \cdot \theta_2(k) + \ldots + a_{2,n}(\chi(k),v(k)) \cdot \theta_2(k)^n + \ldots + a_{q-1,1}(\chi(k),v(k)) \cdot \theta_{q-1}(k) + \ldots + a_{q-1,n}(\chi(k),v(k)) \cdot \theta_{q-1}(k)^n + \ldots + a_{q,1}(\chi(k),v(k)) \cdot \theta_q(k) + \ldots + a_{q,n}(\chi(k),v(k)) \cdot \theta_q(k)^n$$

Equation 9

$$m_{g,h}(k) = b_{1,1}(\chi(k),v(k)) \cdot \theta_1(k) + \ldots + b_{1,n}(\chi(k),v(k)) \cdot \theta_1(k)^n + b_{2,1}(\chi(k),v(k)) \cdot \theta_2(k) + \ldots + b_{2,n}(\chi(k),v(k)) \cdot \theta_2(k)^n + \ldots + b_{q-1,1}(\chi(k),v(k)) \cdot \theta_{q-1}(k) + \ldots + b_{q-1,n}(\chi(k),v(k)) \cdot \theta_{q-1}(k)^n + \ldots + b_{q,1}(\chi(k),v(k)) \cdot \theta_q(k) + \ldots + b_{q,n}(\chi(k),v(k)) \cdot \theta_q(k)^n$$

Equation 10 where $a_{i,j}(\chi(k))$ and $b_{i,j}(\chi(k))$ $i=1 \rightarrow q$ are the coefficients for the state $\chi(k)$ of the whole system and the walking speed $v(k)$ and n is the order of the polynomial.

The preferred embodiment uses four localized plantar pressures, thus Equation 9 and Equation 10 become:

$$\theta_{g,h}(k) = a_{1,1}(\chi(k),v(k)) \cdot f_{r1}(k) + \ldots + a_{1,n}(\chi(k),v(k)) \cdot f_{r1}(k)^n + a_{2,1}(\chi(k),v(k)) \cdot f_{r2}(k) + \ldots + a_{2,n}(\chi(k), v(k)) \cdot f_{r2}(k)^n + a_{3,1}(\chi(k),v(k)) \cdot f_{r3}(k) + \ldots + a_{3,n}(\chi(k),v(k)) \cdot f_{r3}(k)^n + a_{4,1}(\chi(k),v(k)) \cdot f_{r3}(k) + \ldots + a_{4,n}(\chi(k),v(k)) \cdot f_{r3}(k)^n$$

Equation 11

$$m_{g,h}(k) = b_{1,1}(\chi(k),v(k)) \cdot f_{r1}(k) + \ldots + b_{1,n}(\chi(k),v(k)) \cdot f_{r1}(k)^n + b_{2,1}(\chi(k),v(k)) \cdot f_{r2}(k) + \ldots + b_{2,n}(\chi(k),v(k)) \cdot f_{r2}(k)^n + b_{3,1}(\chi(k),v(k)) \cdot f_{r3}(k) + \ldots + b_{3,n}(\chi(k),v(k)) \cdot f_{r3}(k)^n + b_{4,1}(\chi(k),v(k)) \cdot f_{r3}(k) + \ldots + b_{4,n}(\chi(k),v(k)) \cdot f_{r3}(k)^n$$

Equation 12 where $a_{i,j}(\chi(k))$ and $b_{i,j}(\chi(k))$ $i=1 \rightarrow q$ are the coefficients for the state $\chi(k)$ of the whole system and the walking speed $v(k)$ and n is the order of the polynomial Since all the kinetic/kinematic parameters $\theta_{kn}(k)$ and $m_{kn}(k)$ are computed from non-complex mathematical relationships, the computation of the trajectory is simple and fast and can be calculated by a non-sophisticated electronic circuit board.

Figure 19:
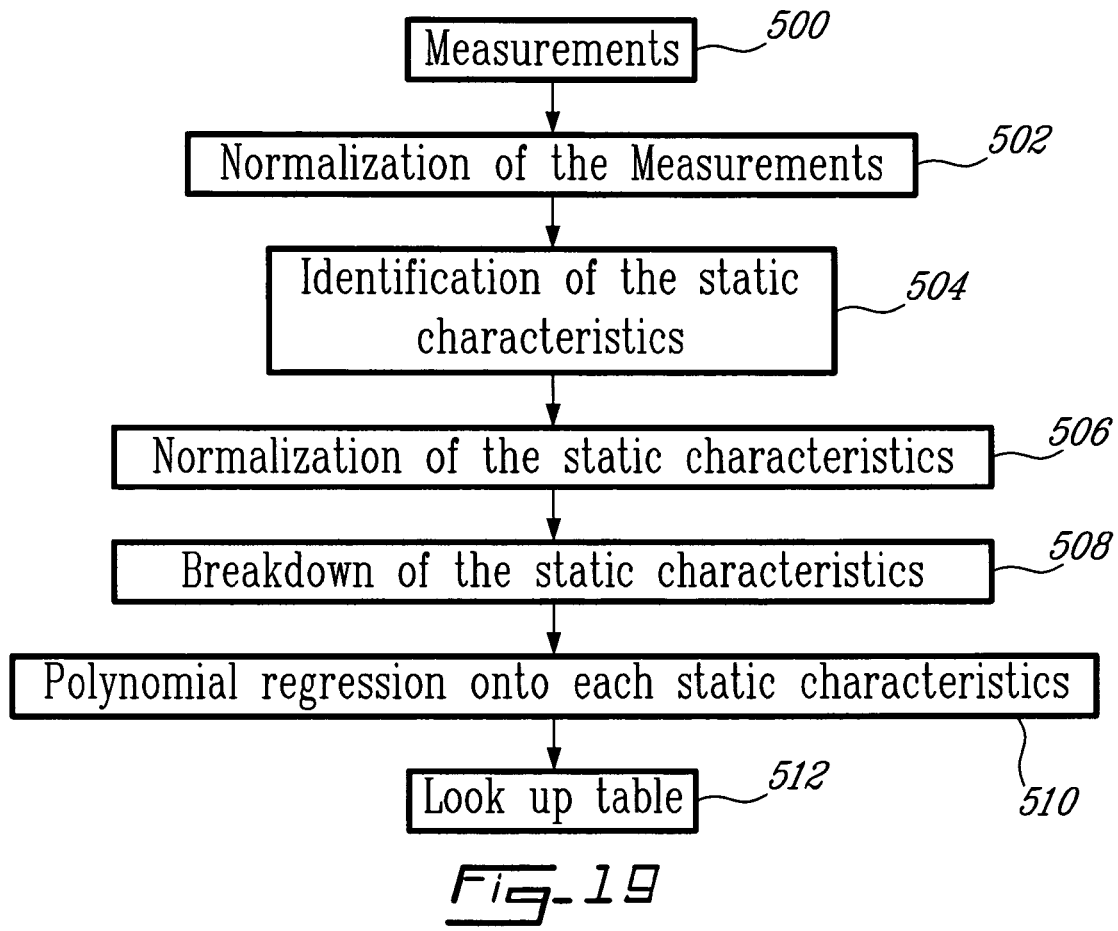
FIG. 19 is a block diagram showing the creation of the Trajectory Generator (TG) lookup table.

The mathematical relationships (time-dependent equations and static characteristics) used in these non-complex mathematical relationships are contained in a lookup table referenced at block 404. FIG. 19 shows a flow chart that depicts the algorithm used to create the TG lookup table. The sequence of steps composing the algorithm is indicated by the sequence of blocks 100 to 512. At block 100, the algorithm measures the selected phenomelogical parameters, which in the preferred embodiment are the localized plantar pressures, and the kinetic/kinematic parameters $\theta_{kn}(k)$ and $m_{kn}(k)$ of a subject. The measured phenomelogical parameters are then normalized in function of the subject's weight. At block 104, the static characteristics linking the phenomelogical parameters to the kinetic/kinematic parameters and the time-dependent equations linking to the time are identified and are then normalized at block 106. Then at block 108, the mathematical relationships (time-dependent equations and static characteristics) are broken down according to the phenomelogical parameters, the phases of locomotion portion, portions of locomotion, the speed of the subject and in the case were Equation 11 and Equation 12 are linear functions, the binary formatted data signals. For each set of mathematical relationships (time-dependent equations and static characteristics) created by the breakdown, a polynomial regression is applied, at block 510, to the mathematical relationships (time-dependent equations and static characteristics) contained in the set. Finally, at block 512, the results of the polynomial regressions are stored in the lookup table and are indexed according to the breakdown of block 108.

The method for building this TG lookup table depicted by the flow chart of FIG. 19 may be applied to any equations belonging to the following analytical/logical family of functions:

$$y_{g,h} = a_0 + a_1 x_1 + a_2 x_1^2 + \ldots + a_n x_1^n + b_0 + b_1 x_2 + b_2 x_2^2 + \ldots + b_m x_2^m + \ldots$$
$$\beta_0 + \beta_1 x_\chi + \beta_2 x_\chi^2 + \ldots + \beta_\eta x_\chi^\eta$$

$$y_{g,h} = \sum_{i=0}^{n} a_i x_1^i + \sum_{i=0}^{m} b_i x_2^i + \ldots \sum_{i=0}^{\eta} \beta_i x_\chi^i$$

$$y_{g,h} = \sum_{i=0}^{n_1} a_{1,i} x_1^i + \sum_{i=0}^{n_2} a_{2,i} x_2^i + \ldots \sum_{i=0}^{n_\chi} a_{\chi,i} x_\chi^i$$

$$y_{g,h} = \sum_{j=1}^{\chi} \sum_{i=0}^{n_j} a_{j,i} \cdot x_j^i$$

Equation 13 where
- $y_{g,h}$ is the estimated kinematic ($\hat{\theta}_{g,h}$) or kinetic ($\hat{m}_{g,h}$) variables for the g lower extremities joint through the h plane of motion
- g is the lower extremities joint among the following set: hip, knee, ankle and metatarsophalangeal
- h is the plane of motion among the following set: sagittal, frontal and transversal
- $x_j$ is the $j^{th}$ locomotion related phenomenon, for example the $j^{th}$ localized plantar pressure
- $a_{j,i}$ is the $i^{th}$ coefficient associated the $j^{th}$ locomotion related phenomenon denoted $x_j$
- $n_j$ is the order of the polynomial depicting the $j^{th}$ locomotion related phenomenon denoted $x_j$
- $\chi$ is the number of locomotion related phenomena If it is considered that the family of functions in Equation 13 are dependant on the state of the system they depict, thus following system of equations is obtained:

$$y_{g,h} = \sum_{j=1}^{\chi} \sum_{i=0}^{n_j} a_{j,i}(x) \cdot x_j^i \qquad \text{Equation 14}$$

where

X is the time dependant state vector of the system

In the preferred embodiment, $x_j$ may be substituted by the localized plantar pressures denoted $f_{ri_f}$, where $i_f=[1, \chi]$. In the case of time-dependant equations, $x_j$ may be substituted by the time. Thus, in the case of plantar pressures, Equation 14 becomes:

$$y_{g,h} = \sum_{i_f=1}^{\chi} \sum_{i=0}^{n_{i_f}} a_{i_f,i}(x) \cdot f_{ri_f}^i \qquad \text{Equation 15}$$

where

X is the time dependant state vector of the system

Previously, $y_{g,h}$ has been defined as the estimated kinematic ($\hat{\theta}_{g,h}$) or kinetic ($\hat{m}_{g,h}$) variable for the g lower extremities joints through the h plane of motion. Thus, Equation 15 may be written as:

$$\hat{\theta}_{g,h} = \sum_{i_f=1}^{\chi} \sum_{i=0}^{n_{i_f}} a_{i_f,i}(x) \cdot f_{ri_f}^i \qquad \text{Equation 16}$$

or $$\hat{m}_{g,h} = \sum_{i_f=1}^{\chi} \sum_{i=0}^{n_{i_f}} a_{i_f,i}(x) \cdot f_{ri_f}^i \qquad \text{Equation 17}$$

The goal is the identification of the Equation 16 and Equation 17 functions from a set of $n_s$ samples, obtained from experimentation. A sample contains data related to the locomotion related phenomenon along with the corresponding kinematic ($\theta_{g,h}$) or kinetic ($m_{g,h}$) variables.

The following array of data is obtained from experimentation:

TABLE 17

Data obtained from experimentation

| t | x | $x_1$ | $x_2$ | ... | $x_j$ | ... | $x_\chi$ | $\theta_{g,h}$ | $m_{g,h}$ |
|---|---|---|---|---|---|---|---|---|---|
| 1 | | | | | | | | | |
| 2 | | | | | | | | | |
| ... | | | | | | | | | |
| $i_s$ | | | | ... | $x_{j,is}$ | ... | | | |
| ... | | | | | | | | | |
| $n_s$ | | | | | | | | | | where
- j, $\chi$ is the index and the number of locomotion related phenomena
- $i_s$, $n_s$ is the index and the number of frames
- t is the time [s]
- x is the time dependant state vector of the system
- $x_j$ is the selected locomotion related phenomenon
- $\theta_{g,h}$ is the kinematic variables for the g lower extremities joint through the h plan of motion
- $m_{g,h}$ is the kinetic variable for the g lower extremities joint through the h plan of motion The logical functions $a_{j,i}(X)$ are then presented in the form of a look-up table, as shown in the following example:

TABLE 18

Look-up table example
$a_{j,i}(x)$

| t | x | $a_{1,0}$ | $a_{1,1}$ | ... | $a_{2,0}$ | $a_{2,1}$ | ... | $a_{x,0}$ | $a_{x,1}$ | ... | $a_{x,nx}$ |
|---|---|---|---|---|---|---|---|---|---|---|---|
| 1 | $x_1$ | 34,5 | 23,1 | ... 12,3 | 92,5 | ... 83,6 | 52,4 | ... 72,5 | | | |
| 2 | $x_2$ | 23,6 | 87,5 | ... 64,4 | 84,9 | ... 93,4 | 38,6 | ... 28,5 | | | |
| ... | ... | ... | ... | ... | ... | ... | ... | ... | ... | | |
| $i_c$ | $x_{ic}$ | 76,9 | 82,5 | ... 93,3 | $a_{j,i,ic}$ | ... 37,5 | 82,3 | ... 84,4 | | | |
| ... | ... | ... | ... | ... | ... | ... | ... | ... | ... | | |
| $n_c$ | $x_{nc}$ | 61,4 | 90,6 | ... 72,3 | 26,4 | ... 83,5 | 26,4 | ... 28,6 | | | | where
- $i_c$, $n_c$ index and dimension of the look-up table ($n_c$ is the number of considered where quantized states)
- x is the time dependant state vector of the system Table 18 establishes the relationship between the time dependent state vector of the system, the locomotion related phenomenon and the kinematic and the kinetic variables of the lower extremities joints, which are the following static characteristics:

$$\hat{\theta}_{g,h} = f^\theta(x,x) \qquad \text{Equation 18}$$

$$\hat{m}_{g,h} = f^m(x,x) \qquad \text{Equation 19}$$

The methodology used to identify the parameters $a_{j,i}(X)$ is based on the application of a curve-fitting algorithm to a set of data provided from experimentation on human subjects. This experimentation is performed in a laboratory environment under controlled conditions, yielding a set of data in the form of an array, as shown in Table 17.

The curve-fitting algorithm is used to obtain the parameters $a_{j,i}(X)$ for every given time dependant state vector X. This data is used to construct the look-up table, as shown in Table 18.

Figure 20:
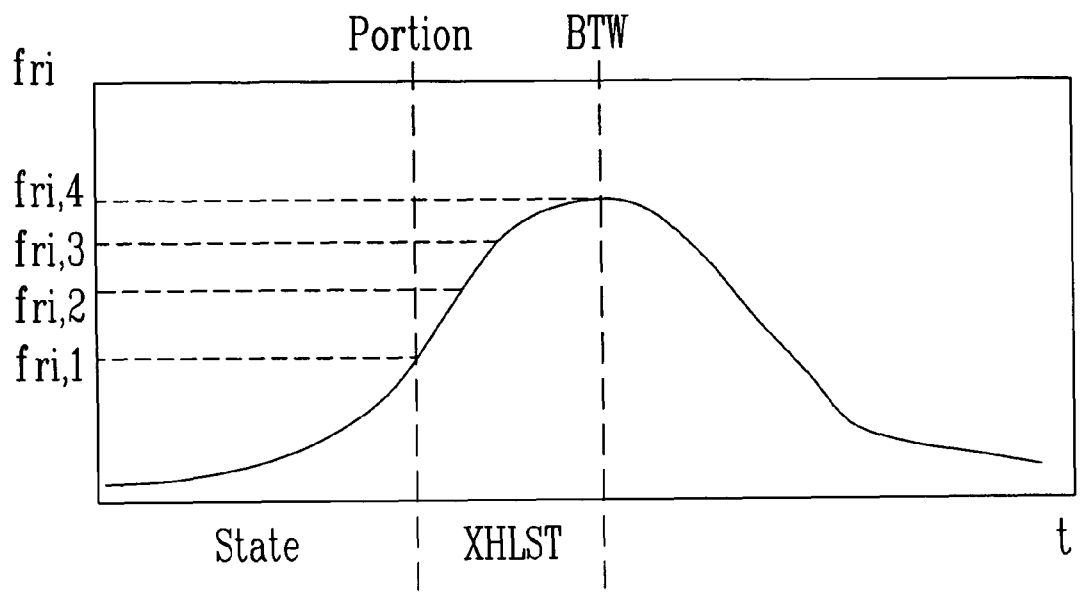
FIG. 20 is a graph showing an example of curve representing a kinematic or kinetic variable for a given portion of locomotion, phase of locomotion portion and subject's speed.
Figure 21:
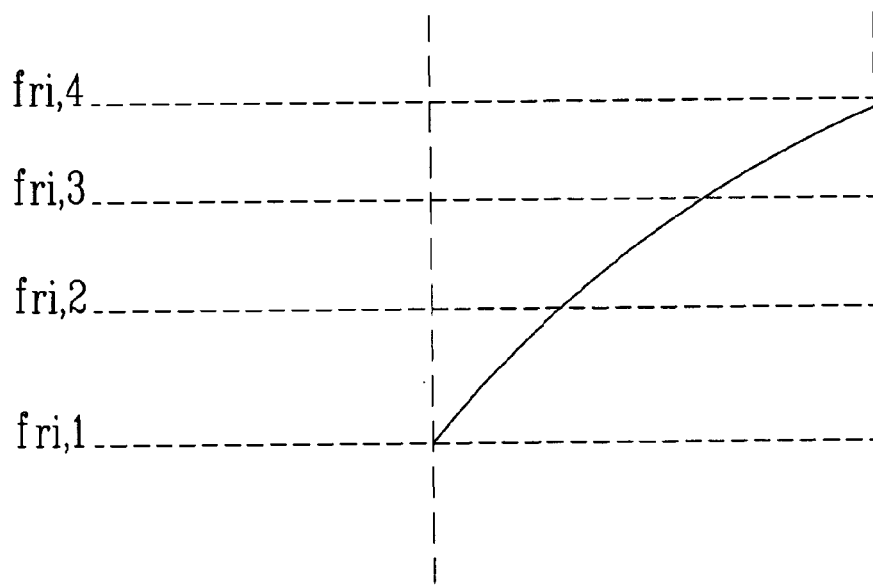
FIG. 21 is an enlarged representation of FIG. 20.

An example of configuration for the method previously described is presented below:

1. the particularities of this configuration are:
  a. the locomotion related phenomenon is composed of a set of four localized plantar pressures supplied by the main artificial proprioceptors;

b. the time dependant state vector is composed of:
  i. the walking speed of the subject;
  ii. the phase of locomotion portion and the portion of locomotion;
  iii. and if Equation 16 and Equation 17 are linear functions:
  iv. the binary formatted magnitude of the four localized plantar pressures;
2. the family of functions depicting the static characteristics $\hat{\theta}_{g,h}=f^\theta(x,x)$ and $\hat{m}_{g,h}=f^m(x,x)$, as described in Equation 16 and Equation 17;
or
  the family of functions depicting the time-dependent equations $\hat{\theta}_{g,h}=f^\theta(x,t)$ and $\hat{m}_{g,h}=f^m(x,t)$, as described in Equation 16 and Equation 17 when $f_{rt_f}$ is substituted by time t.
3. the selected lower extremities joints is the knee joint, which is the joint between the thigh (th) and the shank (sh);
4. the selected plane of motion is the sagittal plane;

In the case where Equation 16 and Equation 17 are linear functions, the time dependant state vector further comprises the binary formatted magnitude of the four localized plantar pressures as added parameters to further segment the curve representing the kinematic ($\theta_{g,h}$) or kinetic ($m_{g,h}$) variables. This is due to the fact that, as shown by FIG. 20, that for a given portion of locomotion, phase of locomotion portion and subject's speed, the curve representing the kinematic ($\theta_{g,h}$) or kinetic ($m_{g,h}$) variables cannot efficiently be approximated by a linear function. To that end, the binary formatted plantar pressures are used to further subdivide the phase of locomotion portion in a number of intervals on which the curve representing the kinematic ($\theta_{g,h}$) or kinetic ($m_{g,h}$) variables may be approximated by linear functions. FIG. 21 is a close-up view of FIG. 20 where it is shown that the curve representing the kinematic ($\theta_{g,h}$) or kinetic ($m_{g,h}$) variables appear relatively linear on each of the added subdivisions. Thus, the use of Equation 16 and Equation 17 which are linear functions entails that the time dependant stated vector will further comprise the binary formatted plantar pressures.

It should be noted that in the preferred embodiment, the lookup table contains mathematical relationships that have been normalized in amplitude. The TG (44) uses the relative value of the localized plantar pressures instead of the magnitude of the signal. This means that the localized plantar pressures are set into a [0, 1] scale for a specific state of the whole system $\chi(k)$. This ensures that the mathematical relationships (time-dependant equations and static characteristics) are independent of the weight of the subject. It is worth to note that, because the TG's architecture use the walking speed as a component of the state of the whole system, the static characteristics lookup table is valid for any walking speed comprised within the operational conditions, which are, in the preferred embodiment, between 84 and 126 steps/min, though the lookup table may be computed for other intervals.

The Regulator (48) uses a control law with a similar structure to control algorithms currently employed in numerous commercial or experimental applications. Various control laws may be implemented in the Regulator (48), examples of which are provided below.

First, the Regulator (48) may use a simple PID control law, which is written as:

$$\mu(t)=k_d\dot{\bar{x}}(t)+k_p\bar{x}(t)+k_i\int\bar{x}dt \qquad \text{Equation 20}$$

where
$k_d$ is the gain associated to the differential component of the regulator
$k_p$ is the gain associated to the proportional component of the regulator
$k_i$ is the gain associated to the integral component of the regulator
$x_i$ is the requested trajectory
$x_o$ is the trajectory performed by the system
$\bar{x}$ is the error between the requested ($x_i$) and performed trajectory ($x_o$)
$\mu$ is the set point intended to the system
applied to the proposed system, that is x=θ or x=m, we have:

$$\mu_{g,h}^x(t)=k_d\dot{\bar{x}}_{g,h}(t)+k_p\bar{x}_{g,h}+k_i\int\bar{x}_{g,h}dt \qquad \text{Equation 21}$$

where
g=[sagittal (sg), frontal (fr), transversal (tr)] is the plane of the motion
h=[hip (hp), knee (kn), ankle (an), metatarsophalangeal (mp)] is the joint
x=θ or m
where the transfer function between the error x and the set-point is expressed as:

$$\frac{\mu_{g,h}^\theta(t)}{\bar{x}_{g,h}(t)}=\frac{b_2\cdot z^2+b_1\cdot z+b_0}{z(z-1)} \qquad \text{Equation 22}$$

where
$b_2=k_i+k_p+k_d$
$b_1=-(k_p+k_d)$
$b_0=k_d$
x=θ or m
in which the corresponding recurrent equation is:

$$\mu_{g,h}^x(k)=\mu_{g,h}^x(k-1)+b_0\bar{x}_{g,h}(k-2)+b_1\bar{x}_{g,h}(k-1)+b_2\cdot\bar{x}_{g,h}(k) \qquad \text{Equation 23}$$

where
k is the current increment
x=θ or m

Secondly, the Regulator (48) may use an adaptive PID control law. The transfer function of an adaptive PID is the same as that of a conventional PID but the parameters $b_2$, $b_1$ and $b_0$ are function of the state of the whole system $\chi(k)$. From Equation 23, the recurrence equation of the adaptive PID is:

$$\mu_{g,h}^x(k)=\mu_{g,h}^x(k-1)+b_0(\chi(k))\cdot\bar{x}_{g,h}(k-2)+b_1(\chi(k))\cdot\bar{x}_{g,h}(k-1)+b_2(\chi(k))\cdot\bar{x}_{g,h}(k) \qquad \text{Equation 24}$$

where
k is the current increment
x=θ or m

Thirdly, the Regulator (48) may use a conventional PID with measured moment, which may be written as:

$$f_{g,h}^\mu(k)=f_{g,h}^m(k)+\bar{f}_{g,h}(k) \qquad \text{Equation 25}$$

where
$f_{g,h}^m(k)$ is the force measured at the joint
$\bar{f}_{g,h}(k)$ is the force generated by the regulator
$f_{g,h}^\mu(k)$ is the set point of the force intended to the joint
From Equation 22, the transfer function between the position error $\bar{x}_{g,h}$ and the force set-point $\bar{f}_{g,h}(k)$ is expressed as:

$$\frac{\bar{f}_{g,h}(t)}{\bar{x}_{g,h}(t)} = K \cdot \left( \frac{b_2 \cdot z^2 + b_1 \cdot z + b_0}{z(z-1)} \right) \quad \text{Equation 26}$$

where
K is the gain yielded by the device between the position and the force set point
x=θ or m
Thus, the recurrent equation of the final force set point $f_{g,h}{}^H(k)$ is given by the following relationship:

$$f_{g,h}{}^H(k) = f^m(k) + \bar{f}_{g,h}(k-1) + b_0 \bar{x}_{g,h}(k-2) + b_1 \bar{x}_{g,h}(k-1) + b_2 \cdot \bar{x}_{g,h}(k) \quad \text{Equation 27}$$

where
k is the current increment
x=θ or m

What is claimed is:

1. A method of controlling an actuated prosthesis of an amputee, the actuated prosthesis comprising an electric actuator, a first limb member, and a second limb member distally located from a stump-socket member with respect to the first limb member, the method comprising:
  receiving information in real-time from a plurality of artificial proprioceptors located within or on a prosthetic foot about dynamics of the amputee's movement, wherein the prosthetic foot replaces a missing foot of the amputee;
  processing said information with a control system to determine a relative vertical direction of a locomotion activity, wherein the control system is located within or on the actuated prosthesis, wherein the first limb member replaces at least a portion of a first missing limb of the amputee and the second limb member replaces at least a portion of a second missing limb of the amputee, and wherein the first limb member and the second limb member are coupled together to form a pivot and are distally located from the stump-socket member with respect to a proximal connector configured to operatively attach the actuated prosthesis to the stump-socket member;
  determining a required force and/or torque to be applied to the second limb member based at least in part on the determined relative vertical direction of the locomotion activity;
  outputting a signal from the control system to a power drive based at least in part on the determined required force and/or torque; and
  supplying electrical power to the electric actuator from an electric power supply distally located from the stump-socket member with respect to the proximal connector based at least in part on the signal received by the power drive, wherein the power drive controls the amount of electrical power provided to the electric actuator from the electric power supply,
  wherein the electric actuator is distally located from the stump-socket member with respect to the proximal connector, is coupled to the first limb member and the second limb member posterior to the pivot, and affects force and/or torque between the first and second limb members during gait, and wherein there is only one powered actuator between the proximal connector and the second limb member.

2. The method of claim 1, further comprising processing said information with the control system to determine a progression within the locomotion activity of the amputee's movement, wherein said processing comprises using a lookup table to determine the required force and/or torque to be applied by the electric actuator based at least in part on the determined progression within the locomotion activity.

3. The method of claim 1, further comprising processing said information with the control system to determine a walking speed of the amputee, wherein said processing comprises using a lookup table to determine the required force and/or torque to be applied by the electric actuator based at least in part on the determined the walking speed of the amputee.

4. The method of claim 1, wherein the relative vertical direction comprises at least one of an incline, a decline, upstairs, and downstairs.

5. The method of claim 1, wherein the actuated prosthesis is a leg prosthesis and wherein the electric actuator is operated to move one or more members of the leg prosthesis.

6. The method of claim 5, wherein the leg prosthesis comprises a knee member that is moved by the electric actuator relative to a trans-tibial member.

7. The method of claim 5, wherein the leg prosthesis comprises an ankle joint.

8. The method of claim 1, wherein the artificial proprioceptors comprise at least a plantar pressure sensor and a gyroscope.

9. A method of controlling an actuated prosthesis of an amputee, the actuated prosthesis comprising a linear actuator, a first limb member, and a second limb member distally located from a stump-socket member with respect to the first limb member, the method comprising:
  receiving information in real-time from one or more artificial proprioceptors located within or on a prosthetic foot about dynamics of the amputee's movement, wherein the prosthetic foot replaces a missing foot of the amputee;
  processing said information with a control system to determine a walking speed of the amputee, wherein the control system is located within or on the actuated prosthesis, wherein the first limb member replaces at least a portion of a first missing limb of the amputee and the second limb member replaces at least a portion of a second missing limb of the amputee, and wherein the first limb member and the second limb member are coupled together to form a pivot and are distally located from the stump-socket member with respect to a proximal connector configured to operatively attach the actuated prosthesis to the stump-socket member;
  determining joint trajectories and a force and/or torque to be applied by the linear actuator to the joint based at least in part on the determined walking speed of the amputee;
  outputting a signal from the control system to a power drive based at least in part on the determined walking speed of the amputee; and
  supplying electrical power to the linear actuator from an electric power supply distally located from the stump-socket member with respect to the proximal connector based at least in part on the signal received by the power drive, wherein the power drive controls the amount of electrical power provided to the linear actuator from the electric power supply,
  wherein the linear actuator is distally located from the stump-socket member with respect to the proximal connector, is coupled to the first limb member and the second limb member posterior to the pivot, and affects force and/or torque between the first and second limb members during gait, and wherein there is only one powered actuator between the proximal connector and the second limb member.

10. The method of claim 9, wherein the walking speed is determined based on data received by plantar pressure sensors.

11. The method of claim 9, wherein the prosthesis comprises a knee member that is moved by the linear actuator relative to a trans-tibial member.

12. The method of claim 9, wherein said determining joint trajectories and the force and/or torque comprises using a lookup table to determine the force and/or torque based at least in part on the determined walking speed.

13. An actuated prosthetic device for an amputee, the device comprising:
   a proximal connector configured to couple to a stump-socket member;
   a first limb portion coupled to the proximal connector and distally located from the stump-socket member with respect to the proximal connector, the first limb portion configured to replace at least a portion of a first missing limb of an amputee;
   a second limb portion coupled to the first limb portion to form a pivot, distally located from the stump-socket member with respect to the proximal connector, and distally located from the stump-socket member with respect to the first limb portion, the second limb portion configured to replace at least a portion of a second missing limb of the amputee;
   an electric actuator coupled to the first limb portion and the second limb portion posterior to the pivot and distally located from the stump-socket member with respect to the proximal connector, the electric actuator configured to affect the force and/or torque between the first and second limb portions during gait, wherein there is only one powered actuator between the proximal connector and the second limb portion;
   an electric power supply distally located from the stump-socket member with respect to the proximal connector, wherein the electric power supply is configured to supply electrical power to the electric actuator based at least in part on a signal received by a power drive, wherein the power drive is configured to control the amount of electrical power provided to the electric actuator from the electric power supply; and
   a control system configured to:
      receive information in real-time from a plurality of artificial proprioceptors located within or on a prosthetic foot about dynamics of the amputee's movement, wherein the prosthetic foot replaces a missing foot of the amputee,
      process said information to determine a relative vertical direction of a locomotion activity,
      determine a force and/or torque to be applied to the second limb portion based at least in part on the determined relative vertical direction of the locomotion activity, and
      output the signal to the power drive based at least in part on the determined force and/or torque.

14. The device of claim 13, wherein the control system is further configured to:
   determine a progression within the locomotion activity of the amputee's movement; and
   utilize a lookup table to determine the force and/or torque to be applied by the electric actuator based at least in part on the determined progression within the locomotion activity.

15. The device of claim 13, further comprising an ankle joint.

16. The device of claim 13, wherein the artificial proprioceptors comprise at least a plantar pressure sensor and gyroscope.

17. An actuated prosthetic device for an amputee, the device comprising:
   a proximal connector configured to couple to a stump-socket member;
   a first limb portion coupled to the proximal connector and distally located from the stump-socket member with respect to the proximal connector, the first limb portion configured to replace at least a portion of a first missing limb of an amputee;
   a second limb portion coupled to the first limb portion to form a pivot, distally located from the stump-socket member with respect to the proximal connector, and distally located from the stump-socket member with respect to the first limb portion, the second limb portion configured to replace at least a portion of a second missing limb of the amputee;
   a linear actuator coupled to the first limb portion and the second limb portion posterior to the pivot and distally located from the stump-socket member with respect to the proximal connector, the linear actuator configured to affect the force and/or torque between the first and second limb portions during gait, wherein there is only one powered actuator between the proximal connector and the second limb portion;
   an electric power supply distally located from the stump-socket member with respect to the proximal connector, wherein the electric power supply is configured to supply electrical power to the linear actuator based at least in part on a signal received by a power drive, wherein the power drive is configured to control the amount of electrical power provided to the linear actuator from the electric power supply; and
   a control system configured to:
      receive information in real-time from a plurality of artificial proprioceptors located within or on a prosthetic foot about dynamics of the amputee's movement, wherein the prosthetic foot replaces a missing foot of the amputee,
      process said information to determine a walking speed of the amputee,
      determine joint trajectories and a force and/or torque to be applied by the linear actuator to the joint based at least in part on the determined walking speed of the amputee, and
      output the signal to the power drive based at least in part on the determined walking speed of the amputee.

18. The device of claim 17, further comprising a knee member, wherein the linear actuator is configured to move the knee member relative to a trans-tibial member.

19. The device of claim 17, further comprising an ankle joint.

20. The device of claim 17, wherein the control system is further configured to determine the walking speed based on data received by plantar pressure sensors.

* * * * *